(12) United States Patent
Hoshiba et al.

(10) Patent No.: US 6,701,219 B2
(45) Date of Patent: Mar. 2, 2004

(54) CONTROL METHOD FOR A LINK ARM MECHANISM AND AN AUTOMATIC CENTRIFUGAL MACHINE EMPLOYING THIS LINK ARM MECHANISM

(75) Inventors: Hideki Hoshiba, Mito (JP); Masahiro Inaniwa, Hitachinaka (JP); Hidetaka Osawa, Hitachinaka (JP); Hiroshi Hayasaka, Hitachinaka (JP)

(73) Assignee: Hitachi Koki Co., Ltd., Tokyo (JP)

(*) Notice: Subject to any disclaimer, the term of this patent is extended or adjusted under 35 U.S.C. 154(b) by 575 days.

(21) Appl. No.: 09/726,438

(22) Filed: Dec. 1, 2000

(65) Prior Publication Data

US 2001/0000353 A1 Apr. 19, 2001

Related U.S. Application Data

(62) Division of application No. 09/266,605, filed on Mar. 11, 1999.

(30) Foreign Application Priority Data

Mar. 19, 1998 (JP) ............................................. 10-70594
Mar. 19, 1998 (JP) ............................................. 10-70607

(51) Int. Cl.$^7$ ............................................. G06F 19/00
(52) U.S. Cl. ......................................... 700/245; 494/37
(58) Field of Search .............................. 494/37; 700/245

(56) References Cited

U.S. PATENT DOCUMENTS

| | | | |
|---|---|---|---|
| 3,151,073 A | 9/1964 | Anthon | 494/1 |
| 3,317,125 A | 5/1967 | Holden | 494/10 |
| 3,635,394 A | 1/1972 | Natelson | 494/7 |
| 3,722,790 A | 3/1973 | Natelson | 494/11 |
| 4,735,776 A | 4/1988 | Yamamoto et al. | 422/65 |
| 4,927,545 A | 5/1990 | Roginski | 210/745 |
| 4,941,866 A | 7/1990 | Gorodissky et al. | 494/14 |
| 5,242,371 A | 9/1993 | Sato et al. | 494/16 |
| 5,505,684 A | 4/1996 | Piramoon | 494/16 |
| 5,538,493 A | 7/1996 | Gerken et al. | 494/16 |
| 5,551,941 A | 9/1996 | Howell | 494/16 |
| 5,721,676 A | 2/1998 | Bolden et al. | 700/3 |
| 5,730,697 A | 3/1998 | Auchinleck | 494/20 |
| 5,814,276 A | 9/1998 | Riggs | 422/65 |

FOREIGN PATENT DOCUMENTS

JP   58-160081   9/1983

*Primary Examiner*—Leo Picard
*Assistant Examiner*—Sheela S. Rao
(74) *Attorney, Agent, or Firm*—Louis Woo

(57) ABSTRACT

An automatic centrifugal machine comprises a handling apparatus for shifting a test specimen from a predetermined position, a rotor equipped with a bucket accommodating the test specimen, a drive motor for rotating the rotor, a chamber surrounding the rotor, and a refrigerator for cooling the chamber, and the automatic centrifugal machine has a height equal to or less than 1,450 mm. A conveyor line, conveying the test specimen, has a height in a range from 750 mm to 850 mm. The handling apparatus of the test specimen is formed by a link arm mechanism including first and second sliders, first and second arms, and a manipulator hand. The manipulator hand is shifted by controlling first and second sliders so as to satisfy the following relationship $$Bx = x1 - \sqrt{L2^2 - \left[L1 \sin\left\{\cos^{-1}\left(\frac{x1 - Ax}{L1}\right)\right\} + d\right]^2}$$

where "L1" represents the length of a first arm, "L2" represents the length of a second arm, "d" represents the clearance between the arm pivot axes on the first and second sliders, "Ax" represents the position of the first slider in the sliding direction and "Bx" represents the position of the second slider in the sliding direction, and "x1" represents the position of the shift member in the sliding direction.

4 Claims, 19 Drawing Sheets

CONTROL METHOD FOR A LINK ARM MECHANISM AND AN AUTOMATIC CENTRIFUGAL MACHINE EMPLOYING THIS LINK ARM MECHANISM

This is a division of application Ser. No. 09/266,605, filed Mar. 11, 1999.

BACKGROUND OF THE INVENTION

The present invention relates to a control method for a link arm mechanism which is preferably used as a handling mechanism for shifting a test specimen. Furthermore, the present invention relates to a centrifugal operation system comprising an automatic centrifugal machine and an associated conveyor line. The automatic centrifugal machine employs the link arm mechanism for transporting the test specimen from the conveyor line to a rotor to perform a centrifugal separation.

Unexamined Japanese patent application No. 58-160071 discloses a conventional link arm mechanism comprising a shift member (i.e., a mechanical hand) supported by two sliders shiftable in parallel with each other.

SUMMARY OF THE INVENTION

An object of the present invention is to provide a control method for the link arm mechanism.

Another object of the present invention is to provide a centrifugal operation system comprising an automatic centrifugal machine and a conveyor line, which is capable of automatically transporting the test specimen from the conveyor line to a rotor of the automatic centrifugal machine or vice versa.

In order to accomplish this and other related objects, a first aspect of the present invention provides a control method for a link arm mechanism. The link arm mechanism comprises a first guide member and a second guide member disposed in parallel with each other. A first slider is shiftable along the first guide member. A second slider is shiftable along the second guide member. A first arm has the length longer than a clearance between axes of the first guide member and the second guide member. The first arm has one end pivotally supported by the first slider. A second arm has the length longer than the clearance between the axes of the first guide member and the second guide member. The second arm has one end pivotally supported by the second slider. A shift member, supporting a working device, is supported by the other ends of the first and second arms.

The method for controlling this link arm mechanism comprises the step of shifting the shift member along a line normal to the sliding direction of the first and second sliders by controlling the sliding positions of the first and second sliders so as to satisfy the following relationship $$Bx = x1 - \sqrt{L2^2 - \left[L1 \sin\left\{\cos^{-1}\left(\frac{x1-Ax}{L1}\right)\right\} + d\right]^2}$$

where "L1" represents the length of the first arm, "L2" represents the length of the second arm, "d" represents the clearance between the arm pivot axes on the first slider and the second slider, "Ax" represents the position of the first slider in the sliding direction and "Bx" represents the position of the second slider in the sliding direction, and "x1" represents the position of the shift member in the sliding direction.

Preferably, the control step for shifting the shift member comprises a calculating step for obtaining a target speed curve of the first slider and a target speed curve of the second slider based on a target speed curve of the shift member.

Preferably, an angle sensor is provided at least at one of the first and second sliders to detect the shifting position of the shift member based on a detected angle of the angle sensor.

Preferably, the control step for shifting the shift member is performed periodically, and the detection of the shifting position of the shift member is performed at least before or after each shifting operation of the shift member.

A second aspect of the present invention provides a centrifugal operation system comprising an automatic centrifugal machine and an associated conveyor line. The automatic centrifugal machine comprises a handling apparatus for shifting a test specimen from a predetermined position, a rotor equipped with a bucket accommodating the test specimen, a drive motor for rotating the rotor, a chamber surrounding the rotor, and a refrigerator for cooling the chamber. The height of this automatic centrifugal machine is equal to or less than 1,450 mm. The conveyor line is for conveying the test specimen, and the height of this conveyor line is in a range from 750 mm to 850 mm.

Preferably, the refrigerator is disposed under the drive motor. The handling apparatus comprises a guide member disposed along a line normal to a rotational axis of the drive motor, a slider shiftable along the guide member, and an arm having one end pivotally connected to the slider and the other end pivotally connected to a shift member. The shift member is equipped with a manipulator hand for holding the test specimen.

Preferably, the drive motor performs a high-speed rotational operation for rotating the rotor at high speeds to give a centrifugal force to the test specimen and also performs a low-speed rotational operation for determining an angular position of the rotor when the rotor is stopped.

Preferably, the drive motor is a servo motor.

Preferably, the automatic centrifugal machine comprises a controller connected to an external control apparatus via a communication cable to control the operation of the automatic centrifugal machine in accordance with a command sent from the external control apparatus.

BRIEF DESCRIPTION OF THE DRAWINGS

The above and other objects, features and advantages of the present invention will become more apparent from the following detailed description which is to be read in conjunction with the accompanying drawings, in which.

DESCRIPTION OF THE PREFERRED EMBODIMENTS

Figure 1:
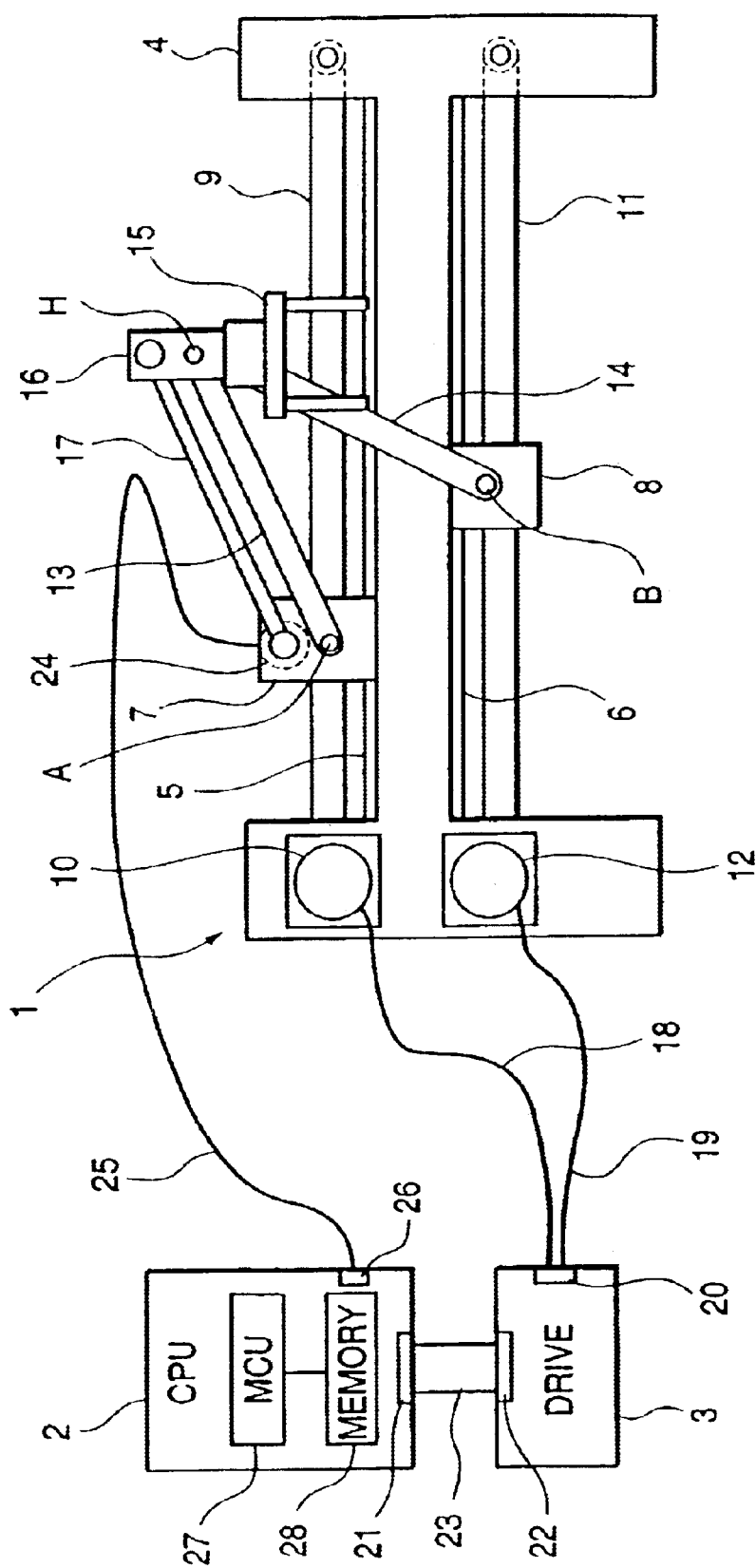
FIG. 1 is a schematic view showing the overall system arrangement of a link arm mechanism and a control apparatus in accordance with a first embodiment of the present invention.

Preferred embodiments of the present invention will be explained with reference to the attached drawings. Identical parts are denoted by the same reference numerals throughout the views.

First Embodiment

Figure 11:
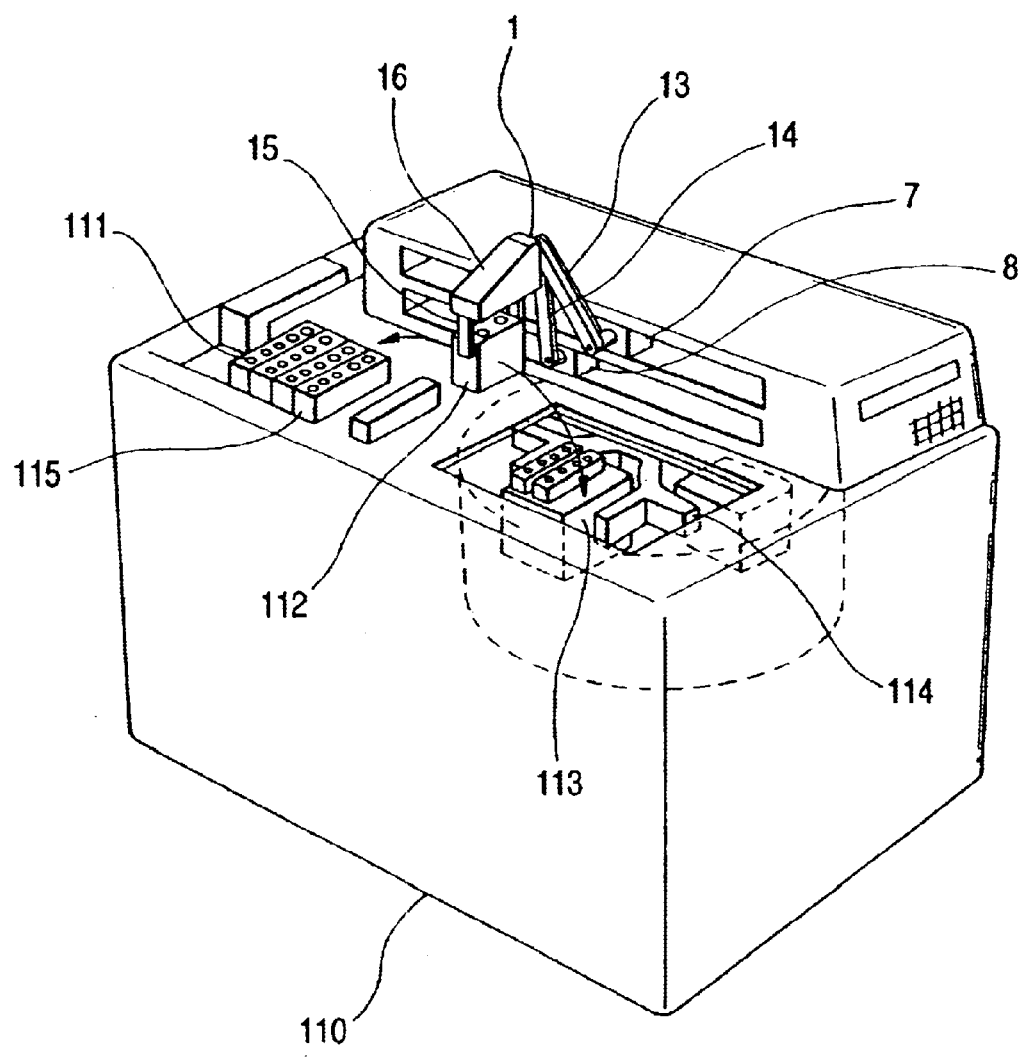
FIG. 11 is a perspective view showing an automatic centrifugal machine in accordance with the first embodiment of the present invention.

FIG. 11 shows an automatic centrifugal machine 110 employing a link arm mechanism 1 controlled by the present invention. The automatic centrifugal machine 110 comprises a manipulator hand 15 supported by a shift member 16. The manipulator hand 15 holds a rack 112. The rack 112 accommodates a total of five test tubes (e.g., vacuum tubes) 111 each including a specimen of blood. A link arm mechanism 1 shifts the manipulator hand 15 in a predetermined direction to convey the rack 112 to a bucket 113 provided in the body of the automatic centrifugal machine 110. A rotor 114 rotates a predetermined number of racks 112 thus loaded to centrifugally separate the specimen 111. After finishing the centrifugal operation, the manipulator hand 15 takes each rack 112 out of the bucket 113 and places it on a rack storage 115.

In the above-described rack shifting operation, the shift member 16 causes a vertical movement to handle each rack 112.

FIG. 1 shows the arrangement of the link arm mechanism 1 and an associated control system comprising a CPU board 2 and a drive board 3. The link arm mechanism 1 comprises a base 4 having a H-shaped cross section. A first guide member 5 and a second guide member 6, extending in parallel with each other, are provided on this base 4. A first slider 7 slides on the first guide member 5. A second slider 8 slides on the second guide member 6. The first slider 7 is fixed to a timing belt 9. A drive motor 10 has an output shaft with a gear or the like (not shown) to entrain the timing belt 9. The drive motor 10, when rotating, shifts the timing belt 9 in the right-and-left direction. In the same manner, the second slider 8 is fixed to a timing belt 11. A drive motor 12 has an output shaft with a gear or the like (not shown) to entrain the timing belt 11. The drive motor 12, when rotating, shifts the timing belt 11 in the right-and-left direction.

The first slider 7 supports one end "A" of a first arm 13 so as to allow the first arm 13 to swing pivotally. The second slider 8 supports one end "B" of a second arm 14 so as to allow the second arm 14 to swing pivotally. The other end of the first arm 13 and the other end of the second arm 14 are pivoted at the same axis "H" of the shift member 16. The shift member 16 is equipped with the manipulator hand 15. The first and second sliders 7 and 8 are disposed at one side of the shift member 16. A parallel link 17, disposed in parallel with the first arm 13, connects the shift member 16 to the first slider 7. Thus, the shift member 16 is stably held. The drive motors 10 and 12 are connected to a connector 20 of the drive board 3 via the motor cables 18 and 19, respectively. The drive board 3 has another connector 22 connected via a flat cable 23 to a connector 21 of the CPU board 2. The CPU board 2 comprises a microcomputer (abbreviated MCU, hereinafter) 27 and a memory 28. The drive board 3 controls the drive motors 10 and 12.

According to the arrangement of the above-described link arm mechanism 1, the motor cables 18 and 19 are free from breaking because the drive motors 10 and 12 are stationarily fixed to the base 4 independently of the shift movement of the sliders 7, 8 and the shift member 16.

Each of the drive motors 10 and 12 has an electromagnetic lock braking mechanism capable of locking its rotor shaft under a spring force so as to securely hold the position of the drive motors 10 and 12. Thus, it becomes possible to prevent the shift member 16 from falling due to self-weight in case of electric power cut. For easy understanding, the manipulator hand 15 shown in FIG. 1 is drawn at a 90-degree rotated position.

Hereinafter, the operation of the above-described link arm mechanism 1 will be explained with reference to the two-dimensional (orthogonal) coordinate system shown in FIG. 2, wherein an X axis represents the right-and-left direction and a Z axis represents the up-and-down direction.

The point "A" represents the pivot axis on the first slider 7. The point "B" represents the pivot axis on the second slider 8. The point "H" represents the pivot axis on the shift member 16. The length of the first arm 13 is represented by L1. The length of the second arm 14 is represented by L2. An up-and-down (i.e., Z-axis directional) distance between the first slider 7 and the second slider 8 is represented by "d." The point "A" moves along a straight line defined by Z=L1. The point "B" moves along another straight line defined by Z=L1−d. The point "H" is movable in the Z-axis direction from 0 to (L1+L2−d). The angle α represents an inclination of the first arm 13 with respect to the line Z=L1, where −π/2≦α≦sin$^{-1}${(L2−d)/L1}. A point "E" represents an intersection of the line Z=L1 and a perpendicular line drawn from the point "H" to the X axis. A point "F" represents an intersection of the line Z=L1−d and the perpendicular line drawn from the point "H" to the X axis. The line segments "HE", "AE", "HB" and "BF" are represented by the following equations (1) to (4).

$$\overline{HE} = |L1 \cdot \sin \alpha| \quad (1)$$

$$\overline{AE} = |L1 \cdot \cos \alpha| \quad (2)$$

$$\overline{HF} = |L1 \cdot \sin \alpha + d| \quad (3)$$

$$\overline{BF} = \{L2^2 - (L1 \cdot \sin \alpha + d)^2\}^{1/2} \quad (4)$$

When the point "H" shifts along the line X=x1, the coordinates of the points "A" and "B" are represented by (Ax, L1) and ((Bx, L1−d), respectively.

Figure 2:
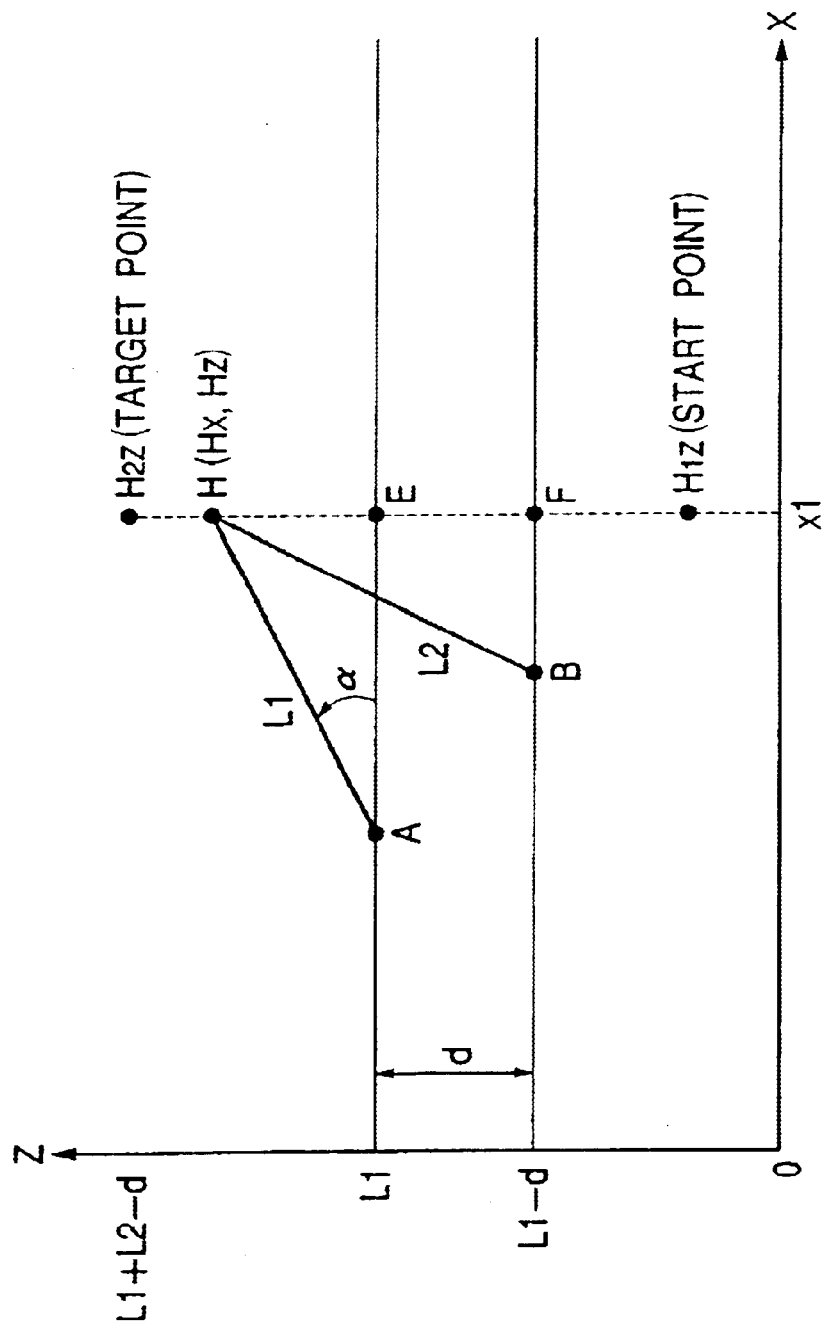
FIG. 2 is a coordinate view illustrating the operation of the link arm mechanism in accordance with the first embodiment of the present invention.

When the sliders 7 and 8 are positioned at the left side of the shift member 16 as shown in FIGS. 1 and 2, the following relationship is established:

$$Ax = x1 - L1 \cdot \cos \alpha \quad (5)$$

$$Bx = x1 - \{L2^2 - (L1 \cdot \sin \alpha + d)^2\}^{1/2} \quad (6)$$

Then, by eliminating a from the equations (5) and (6), the following relationship is obtained.

$$Bx = x1 - \sqrt{L2^2 - \left[L1 \sin\left\{\cos^{-1}\left(\frac{x1 - Ax}{L1}\right)\right\} + d\right]^2} \quad (7)$$

The equation (7) defines the positional relationship between the points "A" and "B" during the vertical movement of the point "H" shifting on the light X=x1.

In other words, controlling the first slider 7 and the second slider 8 so as to satisfy the equation (7) makes it possible to shift the shift member 16 in the vertical direction.

The above-described equations (5) to (7) are replaced by the following equations (5a) to (7a) when the sliders 7 and 8 are positioned at the right side of the shift member 16.

$$Ax = x1 + L1 \cdot \cos \alpha \quad (5a)$$

$$Bx = x1 + \{L2^2 - (L1 \cdot \sin \alpha + d)^2\}^{1/2} \quad (6a)$$

$$Bx = x1 + \sqrt{L2^2 - \left[L1 \sin\left\{\cos^{-1}\left(\frac{-x1 + Ax}{L1}\right)\right\} + d\right]^2} \quad (7a)$$

It is now assumed, as shown in FIG. 2, that the point "H" shifts from a start point H1z to a target point H2z on the vertical line X=x1 for a time T (seconds).

The Z-axis component "Hz" of the point "H" is expressed by the following equation (8).

$$Hz = L1 + L1 \cdot \sin \alpha \quad (8)$$

When the shift member 16 takes the angle α at the time "t", the following relationship is established.

$$Hz = H1z + \frac{(H2z - H1z)}{2}\left(1 - \cos\frac{\pi}{T}t\right) \quad (9)$$

Figure 3:
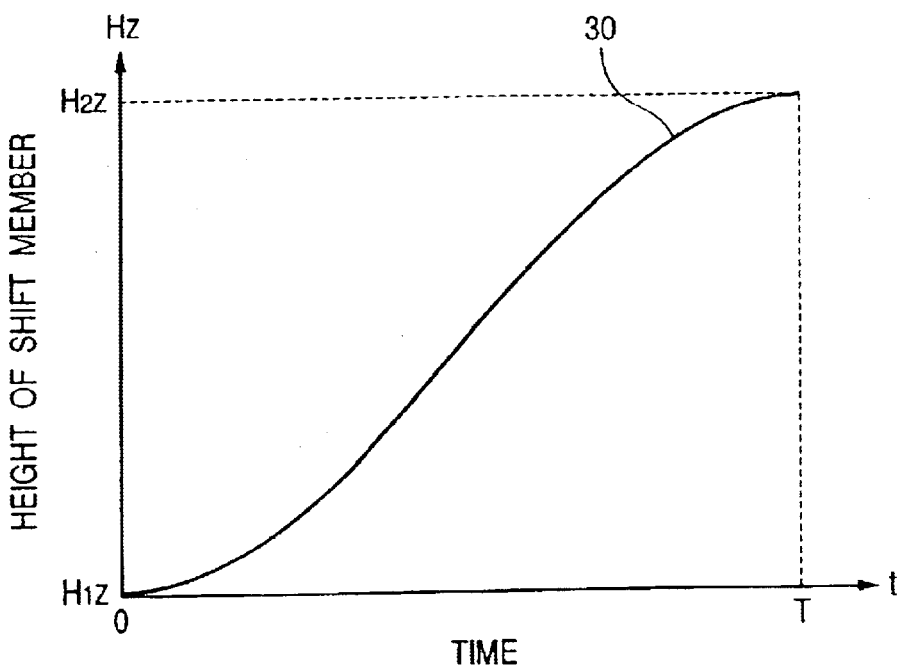
FIG. 3 is a graph showing a relationship between the time and the height of the shift member in accordance with the first embodiment of the present invention.

FIG. 3 shows a curve 30 representing the relationship between the time "t" and the height Hz.

When H2z−H1z=M, the angle α at the time "t" is expressed by the following equation (10).

$$\alpha(t) = \sin^{-1}\left[\frac{1}{L1}\left\{H1z - L1 + \frac{M}{2}\left(1 - \cos\frac{\pi}{T}t\right)\right\}\right] \quad (10)$$

The obtained function α(t) represents the angle α of the shift member 16 shifting in the vertical direction at the time "t".

Figure 4:
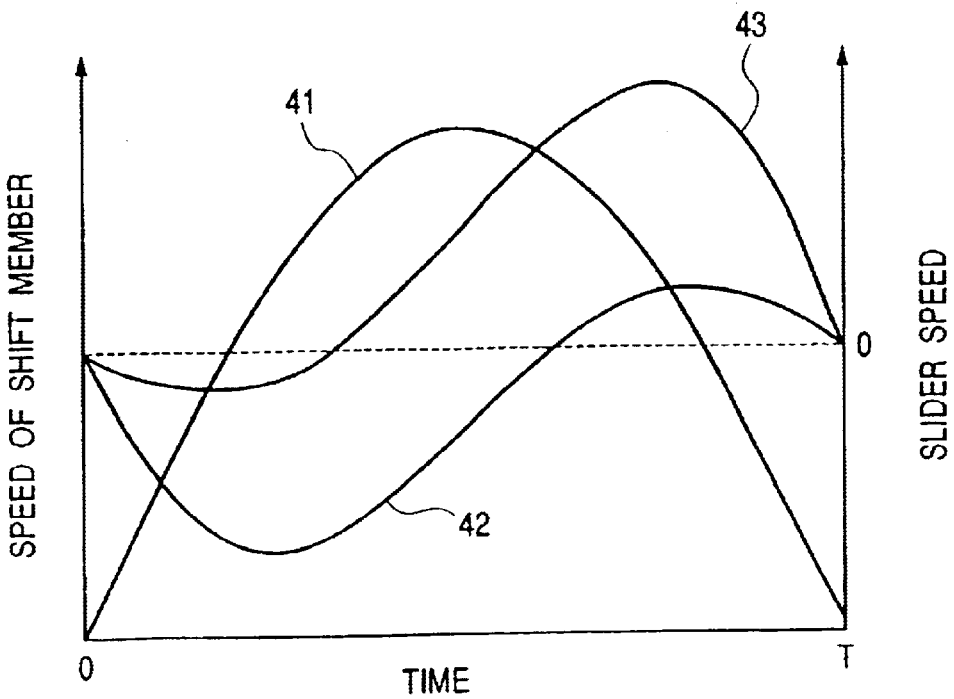
FIG. 4 is a graph showing the relationship between a speed curve of the shift member and a speed curve of each slider in accordance with the first embodiment of the present invention.

FIG. 4 shows a curve 41 representing the speed of the shift member 16 which is a sine wave during a half period. A target (or desirable) speed of the shift member 16 is expressed by this curve 41.

A curve 42 represents the speed of the first slider 7, and a curve 43 represents the speed of the second slider 8.

In the calculation of the speeds of the first and second sliders 7 and 8, it is assumed that the drive motors 10 and 12 are a servo motor equipped with an encoder. The servo motor is generally controlled based on a feedback control of a rotational pulse signal of the encoder. More specifically, the rotational pulse signal of the encoder is detected at predetermined intervals to calculate the target (i.e., command) values of the rotational angle and the angular speed of the servo motor. Then, based on the difference between the command values and the actual data, a PID control data is obtained. The PID control data generally consists of proportional, integral and differential elements. Then, referring to the PID control data thus obtained, each servo motor is driven by the PWM (i.e., pulse width modulation) control. When Δt represents the feedback interval, the time "t" is expressed by the following equation (11).

$$t = t_i = i \cdot \Delta t \ (i=0, 1, 2, \ldots, n) \quad (11)$$

where "i" represents a control number and "n" represents a total number of the feedback controls performed for the shift member 16 which moves from the start point H1z to the target point H2z. The shift time "T" is thus expressed by T=n·Δt.

Figure 5:
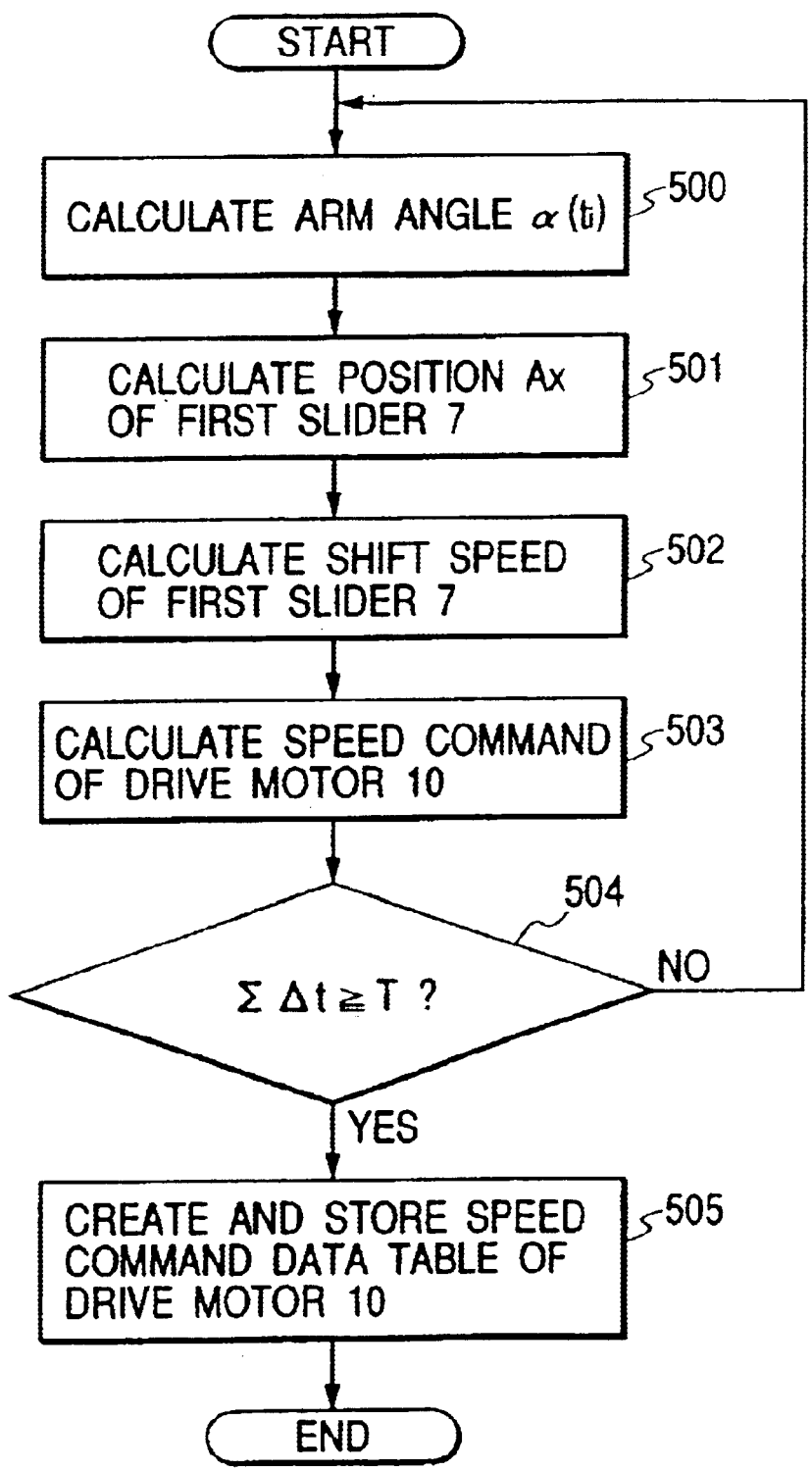
FIGS. 5 and 6 are flowcharts showing the calculation of speed command data of servo motors in accordance with the first embodiment of the present invention.

FIG. 5 shows the calculation procedure for obtaining the speed curve 42 of the first slider 7 based on the target speed curve 41 of the shift member 16.

In a step 500, the arm angle α($t_i$) is calculated based on the equation (10). Then, in a step 501, the position Ax($t_i$) of the first slider 7 is calculated by using the X-axis component xi and the arm angle α($t_i$) of the point "H" into the equation (5).

In a step 502, a positional deviation ΔAx of the first slider 7 during the feedback control interval Δt is calculated based on the following equation (12).

$$\Delta Ax = Ax(t_i) - Ax(t_{i-1}) \quad (12)$$

Then, the shift speed of the first slider 7 is obtained based on the positional deviation ΔAx and the feedback control interval Δt.

In a step 503, a speed command of the drive motor 10 is calculated based on the pitch per rotation of the first slider 7 as well as the shift speed of the first slider 7.

In a step 504, it is checked whether the calculation procedure of the steps 500 to 503 is repeated until the time T has passed (i.e., ΣΔt≧T?).

If the judgement is NO in the step 504, the calculation procedure of the steps 500 to 503 is performed again. If the judgement is YES in the step 504, the calculation procedure proceeds to a step 505. In the step 505, a speed command data table of the drive motor 10 is created. The created speed command data table is stored in the memory 28 of the CPU board 2.

Figure 6:
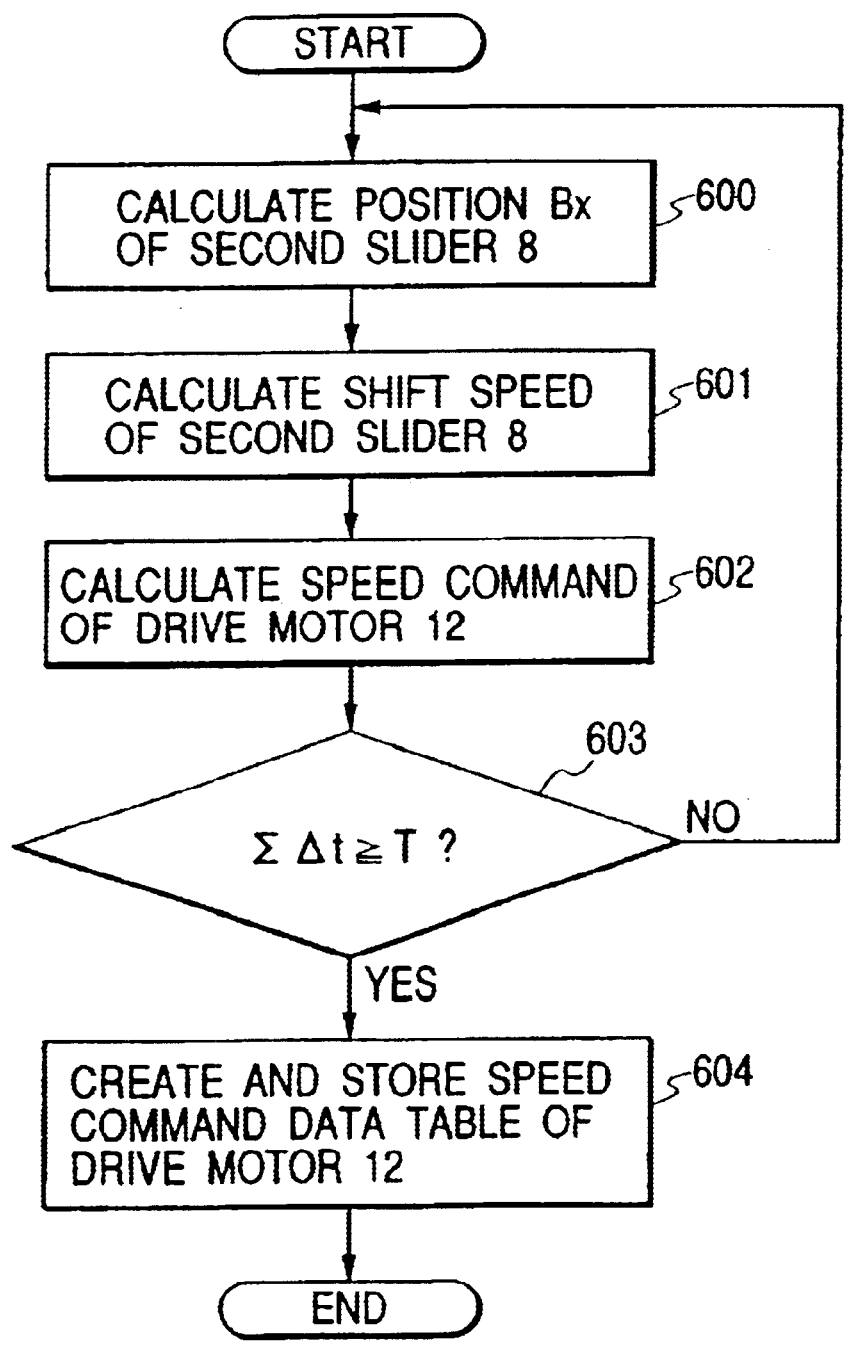

FIG. 6 shows the calculation procedure for obtaining the speed curve 43 of the second slider 8.

In a step 600, the position $Bx(t_i)$ of the second slider 8 is calculated based on the equation (7) by using the X-axis component xi and the position $Ax(t_i)$ of the first slider 7.

In a step 601, apositional deviation $\Delta Bx$ of the second slider 8 during the feedback control interval $\Delta t$ is calculated based on the following equation (13).

$$\Delta Bx = Bx(t_i) - Bx(t_{i-1}) \qquad (13)$$

Then, the shift speed of the second slider 8 is obtained based on the positional deviation $\Delta Bx$ and the feedback control interval $\Delta t$.

In a step 602, a speed command of the drive motor 12 is calculated based on the pitch per rotation of the second slider 8 as well as the shift speed of the second slider 8.

In a step 603, it is checked whether the calculation procedure of the steps 600 to 602 is repeated until the time T has passed (i.e., $\Sigma \Delta t \geq T$?).

If the judgement is NO in the step 603, the calculation procedure of the steps 600 to 602 is performed again. If the judgement is YES in the step 603, the calculation procedure proceeds to a step 604. In the step 604, a speed command data table of the drive motor 12 is created. The created speed command data table is stored in the memory 28 of the CPU board 2.

In the shift control of the shift member 16, the speed command data stored in the memory 28 are successively read out at the predetermined intervals to control the drive motors 10 and 12. The drive motor 10 shifts the first slider 7 in accordance with the optimum speed schedule designated by the speed curve 42. The drive motor 12 shifts the second slider 8 in accordance with the optimum speed schedule designated by the speed curve 43. The MCU 27 performs a time-divisional control for drive the drive motors 10 and 12 independently. The time-divisional control can be realized by alternately switching the tasks during the vertical shift movement of the shift member 16 from the start point H1z to the target height H2z.

When the shift member 16 moves downward from the point H2z to the point H1z, the drive motors 10 and 12 are controlled based on the speed command data read out from the memory 28 in the opposite order. When the shift member 16 moves in the horizontal direction, the drive motors 10 and 12 are driven at the same speed.

The drive motors 10 and 12 may be a stepping motor driven in accordance with a given pulse rate. In this case, each slider shifts in response to one step rotation by an amount equivalent to one step rotation angle. The shift amount $\Delta As$ (=$\Delta Bs$) per step is expressed by the following equation (14).

$$\Delta As = \Delta Bs = \frac{s}{360} \times \frac{1}{N} \times p \qquad (14)$$

where "s" represents a step angle, 1/N represents a speed reduction ratio, and "p" represents a pitch (mm) per rotation.

Under the pulse rate control, each stepping motor stops in a discrete manner. The pulse rate given to the stepping motor is determined through the following calculation.

The target speed (i.e., the curve 41) of the shift member 16 is defined by the equation (9) when the shift member 16 moves from the point "H1z" to the point "H2z". When M represents H1z–H2z, the time "t" is derived from the equation (9).

$$t = \frac{T}{\pi} \cos^{-1}\left\{1 - \frac{2}{M}(Hz - H1z)\right\} \qquad (15)$$

The equation (15) defines the time "t" as a function of the height Hz of the shift member 16.

In calculating the speed curve 42 of the first slider 7, the height Hz of the shift member 16 is expressed by using the position Ax of the first slider 7.

$$Hz = L1 \pm \sqrt{L1^2 - (x1 - Ax)^2} \qquad (16)$$

From the equations (15) and (16), the time "t" is redefined in the following manner.

$$t = \frac{T}{\pi} \cos^{-1}\left[1 - \frac{2}{M}\left\{L1 \pm \sqrt{L1^2 - (x1 - Ax)^2} - H1z\right\}\right] \qquad (17)$$

The equation (17) defines the time "t" as a function of the position Ax of the first slider 7.

The time "t" when the first slider 7 passes a discrete position can be obtained by substituting the discrete position value for the Ax in the equation (17).

In the equations (16) and (17), the sign $\pm$ is selectively used in each case. More specifically, the sign $\pm$ is replaced by + when the height Hz of the point H is higher than the line Z=L1, and replaced by—when lower than the line Z=L1.

In the beginning of the shift movement of the shift member 16, the height Hz of the point H is lower than the line Z=L1. A calculational point "A" is shifted toward the negative direction of the X-axis by the increments of $\Delta As$ until a side $\overline{HE}$ of a right-angled triangle AHE becomes 0. After the height Hz of the point H has reached the level Z=L1, the calculational point "A" is shifted in the opposite (i.e., toward the positive) direction of the X-axis by the increments of $\Delta As$ until the height Hz of the point H reaches the point H2z.

The shifting distance of the point "A" toward the negative direction of the X axis is expressed by the following equation (18).

$$Lan = L1 - \sqrt{L1^2 - (L1 - H1z)^2} \qquad (18)$$

The pulse number required during this shifting operation is obtained by dividing the distance Lan by the shift amount $\Delta As$ (=shift amount per step). The position Ax of the point "A" is obtained from the position Ax–$\Delta As$ of the preceding step. The time "t" is obtained by entering the position Ax into the equation (17). By successively subtracting $\Delta As$ from Ax, each discrete position of the point "A" and the passage time are obtained. The pulse rate is determined based on the time difference during one step.

Figure 7:
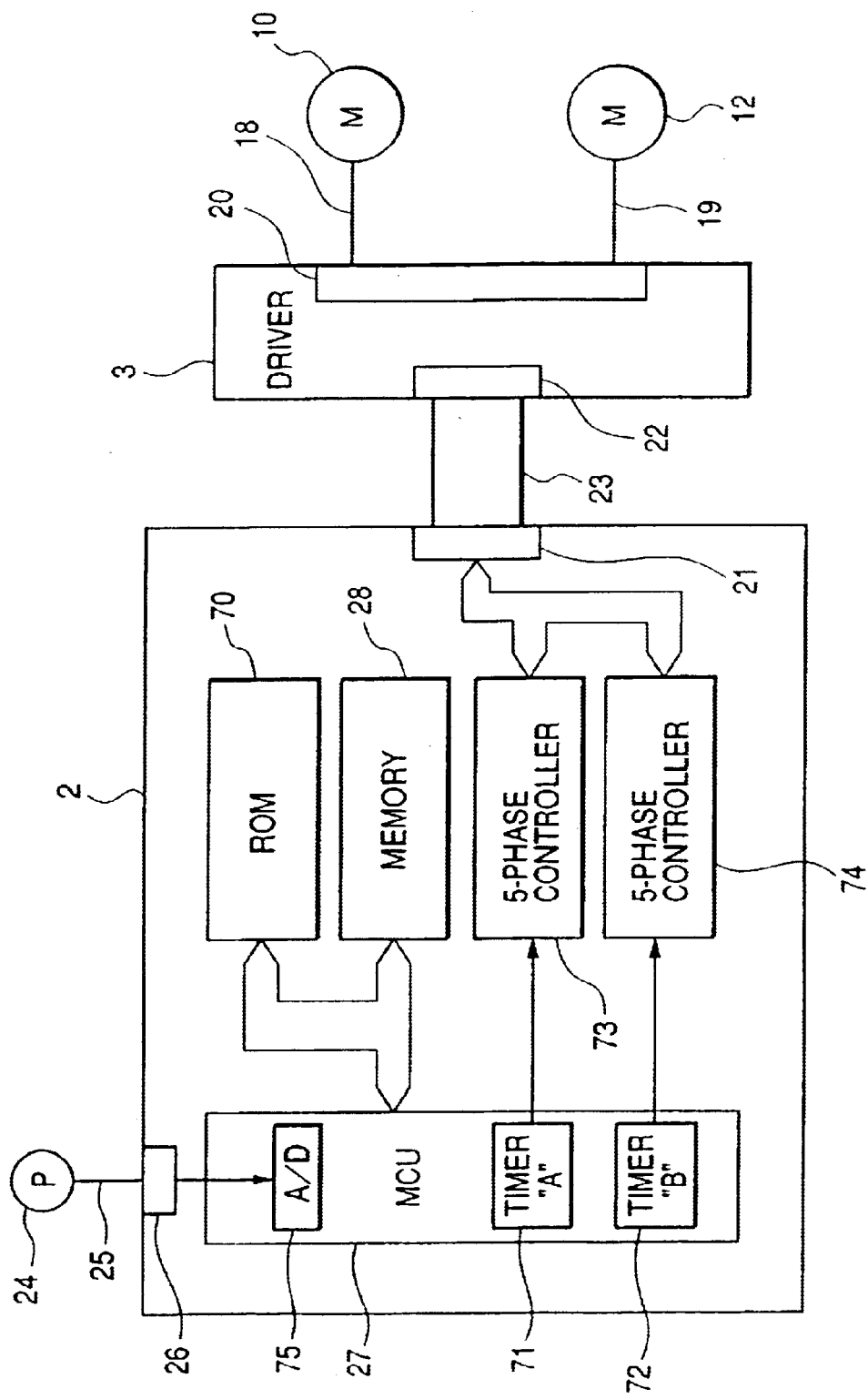
FIG. 7 is a block diagram showing a control system for controlling stepping motors in accordance with the first embodiment of the present invention.

In the pulse generation, the pulse frequency is controlled by using an interrupt function of a timer "A" 71 equipped in the MCU 27 shown in a block circuit of FIG. 7. A timer value At for the interrupt control is defined by the following equation (19).

$$At = \text{(time after one step shifting–time before one step shifting)/(timer clock period)} \qquad (19)$$

Next, the shifting distance of the point "A" toward the positive direction of the X axis is expressed by the following equation (20).

$$Lap = L1 - \sqrt{L1^2 - (H2Z - L1)^2} \quad (20)$$

The pulse number required during this shifting operation is obtained by dividing the distance Lap by the shift amount $\Delta As$ (=shift amount per step). Using the above-described calculation method, the timer value At is similarly obtained based on the time difference during one step shifting. The memory 28 of the CPU board 2 stores the timer value for each shifting in a table.

In calculating the speed curve 43 of the second slider 8, the height Hz of the shift member 16 is defined by using the position Bx of the second slider 8.

$$Hz = (L1 - d) \pm \sqrt{L2^2 - (x1 - Bx)^2} \quad (21)$$

From the equations (15) and (21), the time "t" is redefined as follows.

$$t = \frac{T}{\pi} \cos^{-1}\left[1 - \frac{2}{M}\{L1 - d\} \pm \sqrt{L2^2 - (x1 - Bx)^2} - H1z\}\right] \quad (22)$$

The equation (22) defines the time "t" as a function of the position Bx of the second slider 8.

The time "t" when the second slider 8 passes a discrete position can be obtained by substituting the discrete position value for the Bx in the equation (22).

In the equations (21) and (22), the sign ± is selectively used in each case. More specifically, the sign ± is replaced by + when the height Hz of the point H is higher than the line Z=L1−d, and replaced by—when lower than the line Z=L1−d.

In the beginning of the shift movement of the shift member 16, the height Hz of the point H is lower than the line Z=L1−d. A calculational point "B" is shifted toward the negative direction of the X-axis by the increments of $\Delta Bs$ until a side $\overline{HF}$ of a right-angled triangle BHF becomes 0. After the height Hz of the point H has reached the level Z=L1−d, the calculational point "B" is shifted in the opposite (i.e., toward the positive) direction of the X-axis by the increments of $\Delta Bs$ until the height Hz of the point H reaches the point H2z.

The shifting distance of the point "B" toward the negative direction of the X axis is expressed by the following equation.

$$Lbn = L2 - \sqrt{L2^2 - (L1 - d - H1z)^2} \quad (23)$$

The pulse number required during this shifting operation is obtained by dividing the distance Lbn by the shift amount $\Delta Bs$ (=shift amount per step). The position Bx of the point "B" is obtained from the position Bx−$\Delta Bs$ of the preceding step. The time "t" is obtained by entering the position Bx into the equation (22). By successively subtracting $\Delta Bs$ from Bx, each discrete position of the point "B" and the passage time are obtained. The pulse rate is determined based on the time difference during one step.

In the pulse generation, the pulse frequency is controlled by using an interrupt function of a timer "B" 72 equipped in the MCU 27 shown in the block circuit of FIG. 7. A timer value Bt for the interrupt control is defined by the following equation (24).

$$Bt = (\text{time after one step shifting} - \text{time before one step shifting}) / (\text{timer clock period}) \quad (24)$$

Next, the shifting distance of the point "B" toward the positive direction of the X axis is expressed by the following equation (25).

$$Lbp = L2 - \sqrt{L2^2 - \{H2z - (L1 - d)\}^2} \quad (25)$$

The pulse number required during this shifting operation is obtained by dividing the distance Lbp by the shift amount $\Delta Bs$ (=shift amount per step). Using the above-described calculation method, the timer value Bt is similarly obtained based on the time difference during one step shifting. The memory 28 of the CPU board 2 stores the timer value for each shifting in the table.

There is no difference between the stepping motors and the servo motors in that the sliders 7 and 8 are controlled according to the speed curves 42 and 43 shown in FIG. 4.

Figure 8:
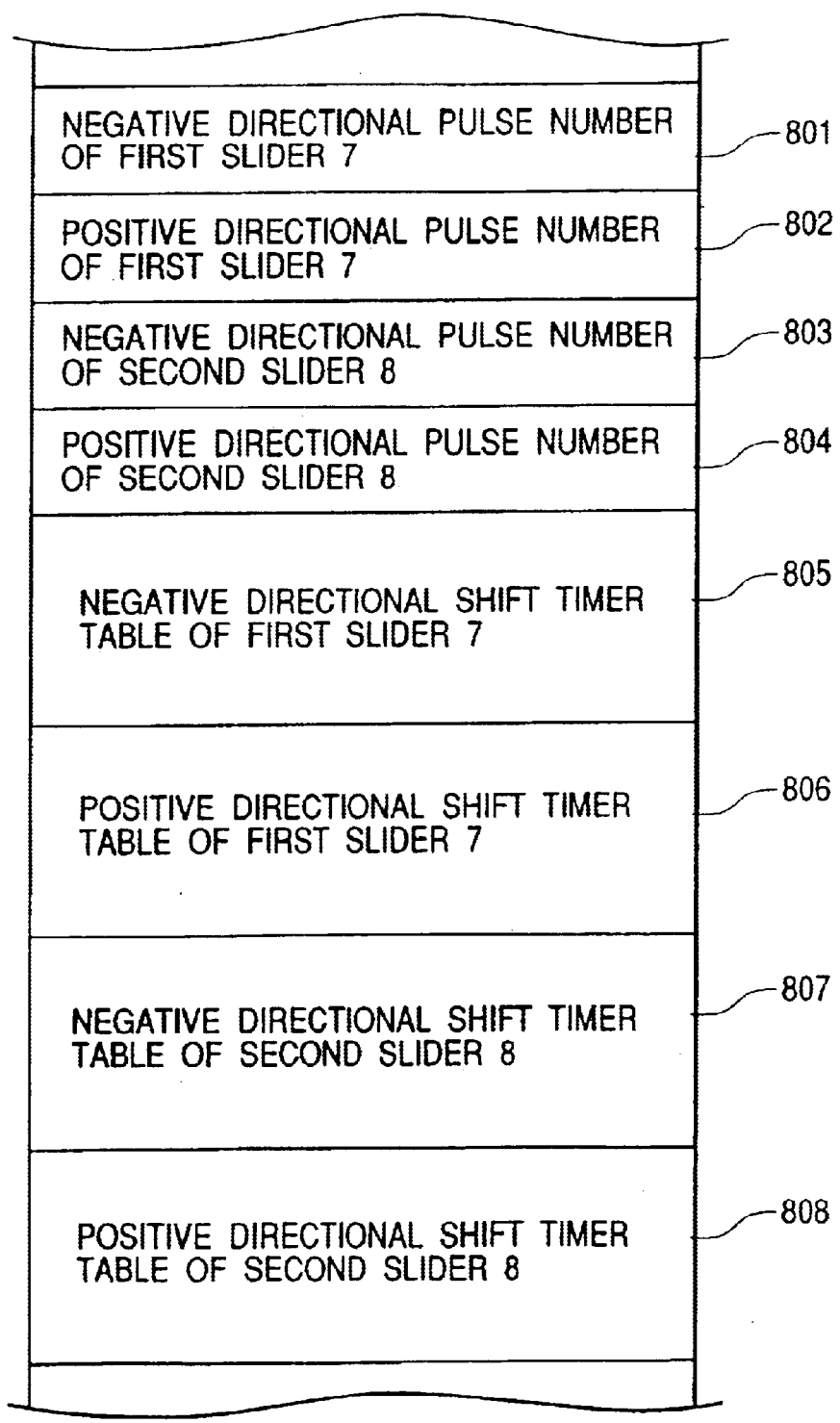
FIG. 8 is a view showing the configuration of a memory storing a timer table used in the control of the stepping motors in accordance with the first embodiment of the present invention.

FIG. 8 shows the details of the data stored in the memory 28. In FIG. 8, numeral 801 represents a negative directional pulse number of the first slider 7. Numeral 802 represents a positive directional pulse number of the first slider 7. Numeral 803 represents a negative directional pulse number of the second slider 8. Numeral 804 represents a positive directional pulse number of the second slider 8. Numeral 805 represents a negative directional shift timer table of the first slider 7. Numeral 806 represents a positive directional shift timer table of the first slider 7. Numeral 807 represents a negative directional shift timer table of the second slider 8. Numeral 808 represents a positive directional shift timer table of the second slider 8.

Figure 9:
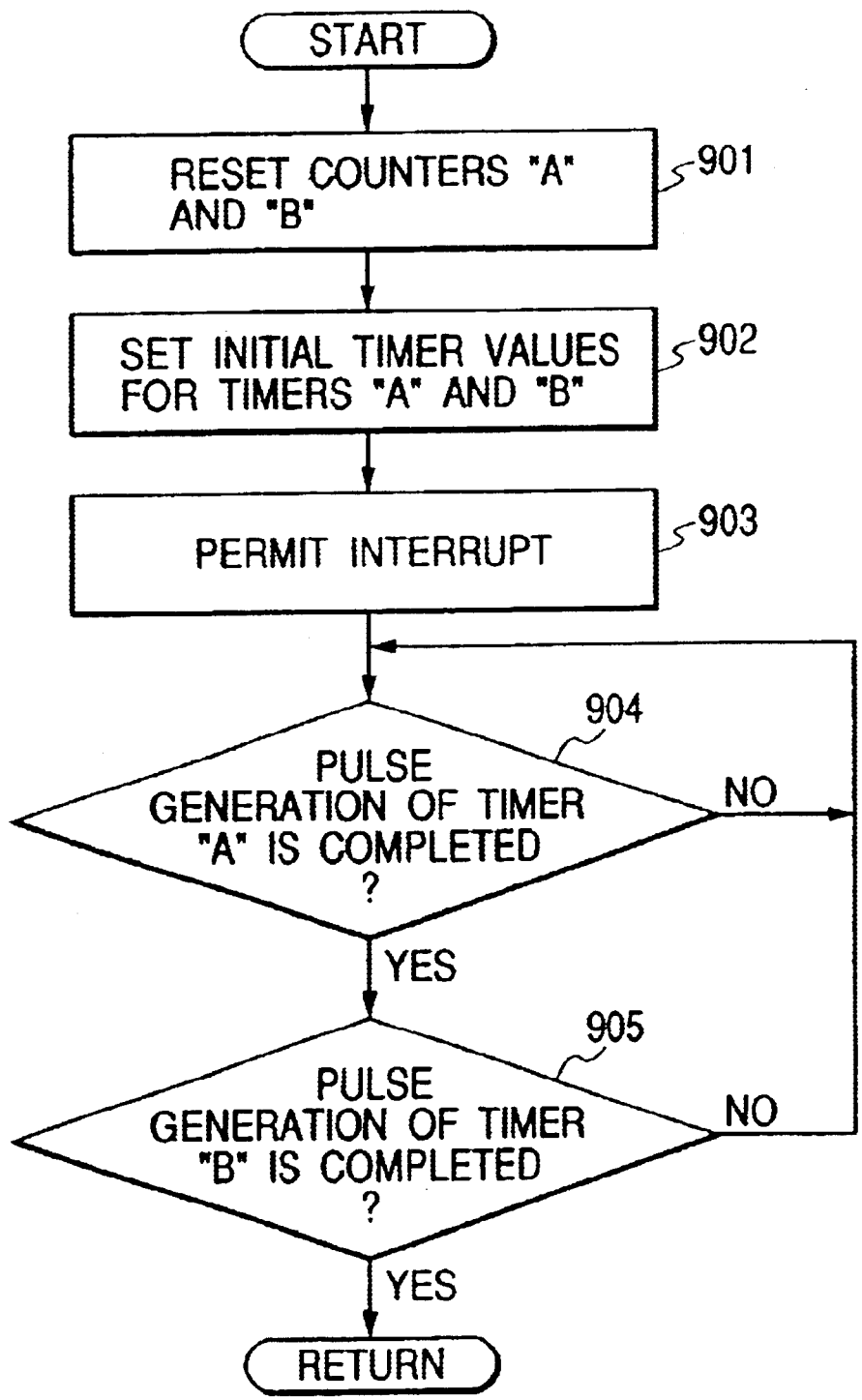
FIG. 9 is a flowchart showing a subroutine used in the control of the stepping motors in accordance with the first embodiment of the present invention.

The upper shifting control of the shift member 16 is performed based on the timer values. FIG. 9 is a flowchart showing a subroutine used in the shifting operation of the shift member 16. In a step 901, counters "A" and "B" are reset in response to rotation of the stepping motor 10 and 12. In a step 902, initial timer values are read out from the memory 28 to set the timer values for the timers "A" and "B". Then, in a step 903, the interrupt processing of the timers "A" and "B" is permitted. In response to the generation of the timer interrupt, the control program starts the interrupt processing.

Figure 10:
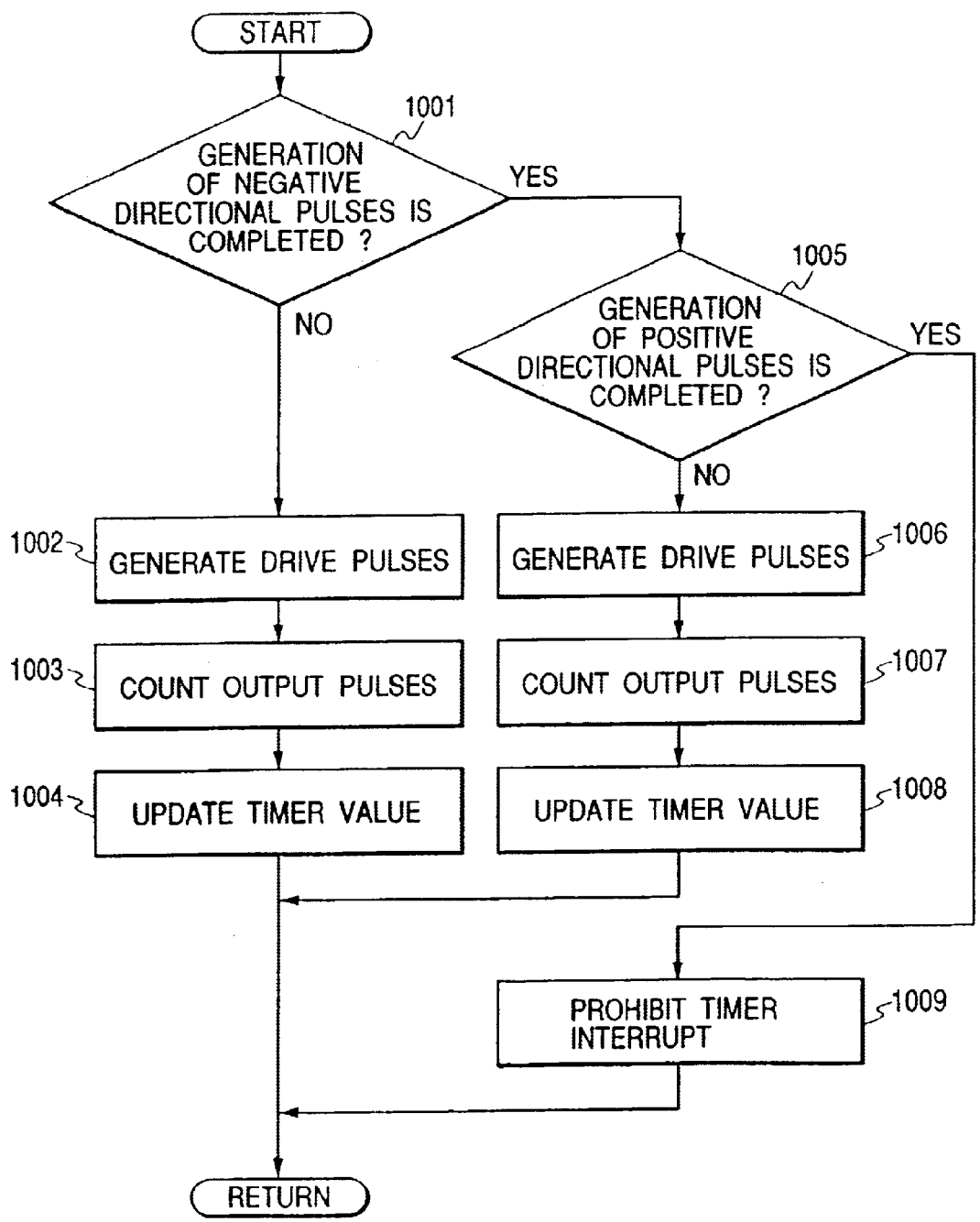
FIG. 10 is a flowchart showing the timer interrupt processing performed in the control of the stepping motors in accordance with the first embodiment of the present invention.

FIG. 10 is a flowchart showing the timer interrupt processing for the upward shifting operation. In a step 1001, it is checked whether the generation of the negative directional pulses is completed. If the judgement is NO in the step 1001, the control flow proceeds to a step 1002 to generate another negative directional drive pulses. Then, in a step 1003, the negative directional output pulses are counted. In a step 1004, a timer value is updated by successively reading out the timer value from the memory 28. The timer value defies the interrupt interval. The above-described steps 1001 to 1004 are performed every interrupt processing until the negative directional pulse generation is finished. The drive pulses are converted into phase switching signals by 5-phase controllers 73 and 74. The driver 33 supplies the drive current to respective drive motors 10 and 12 to rotate them.

When the generation of the negative directional pulses is completed (i.e. YES in the step 1001), generation of the positive directional pulses is subsequently started. More specifically, in a step 1005, it is checked whether the generation of the positive directional pulses is completed. If the judgement is NO in the step 1005, the control flow proceeds to a step 1006 to generate another positive directional drive pulses. Then, in a step 1007, the negative directional output pulses are counted. In a step 1008, the timer value is updated by successively reading out the timer value from the memory 28. These steps 1005 to 1008 are performed every interrupt processing until the positive directional pulse generation is finished. The drive pulses are converted into phase switching signals by 5-phase controllers 73 and 74. The driver 33 supplies the drive current to respective drive motors 10 and 12 to rotate them. When the judgement is YES in the step 1005, the control flow proceeds to a step 1009 to prohibit the timer interrupt.

Then, in a step 904 of the subroutine shown in FIG. 9, it is checked whether the pulse generation of the timer "A" is completed. Subsequently, in a step 905, it is checked whether the pulse generation of the timer "B" is completed. When the judgement result is YES in both of the steps 904 and 905, it is concluded that the upward shifting operation of the shift member 16 is finished.

A read only memory (i.e., ROM) 70 stores the programs used in the above-described shifting operation. Through the above-described control method, the shift member 16 vertically shifts from the original height H1z to the target height H2z. When the shift member 16 moves downward from the point H2z to the point H1z, the drive motors 10 and 12 are controlled based on the timer values read out from the memory 28 in the opposite order. When the shift member 16 moves in the horizontal direction, the drive motors 10 and 12 are driven at the same pulse rate.

In the case of servo motors equipped with an absolute value encoder, it is possible to detect the positions of the sliders 7 and 8 based on the rotational angles of respective drive motors. Thus, the height of the shift member 16 can be calculated anytime based on the positions of the sliders 7 and 8. However, in the case of stepping motors, their rotational angles are unknown at the beginning of the operation. It is therefore impossible to detect the height of the shift member 16 immediately after the electric power is supplied.

To solve this problem, an angle sensor 24 is provided coaxially with the pivot axis of the parallel link 17 of the first slider 7 which constitutes the link arm mechanism 1 as shown in FIG. 1. The angle sensor 24 detects an intersecting angle α between the first arm 13 and the first guide member 5. As the length L1 of the first arm 13 is known, the height of the shift member 16 is obtained from the equation (8). Preferably, the angle sensor 24 is a potentiometer which is connected via a cable 25 and a connector 26 to the CPU board 2. An A/D converter 75, associated with the MCU 27, converts the entered angle signal into a digital data processible in the MCU 27.

Figure 12:
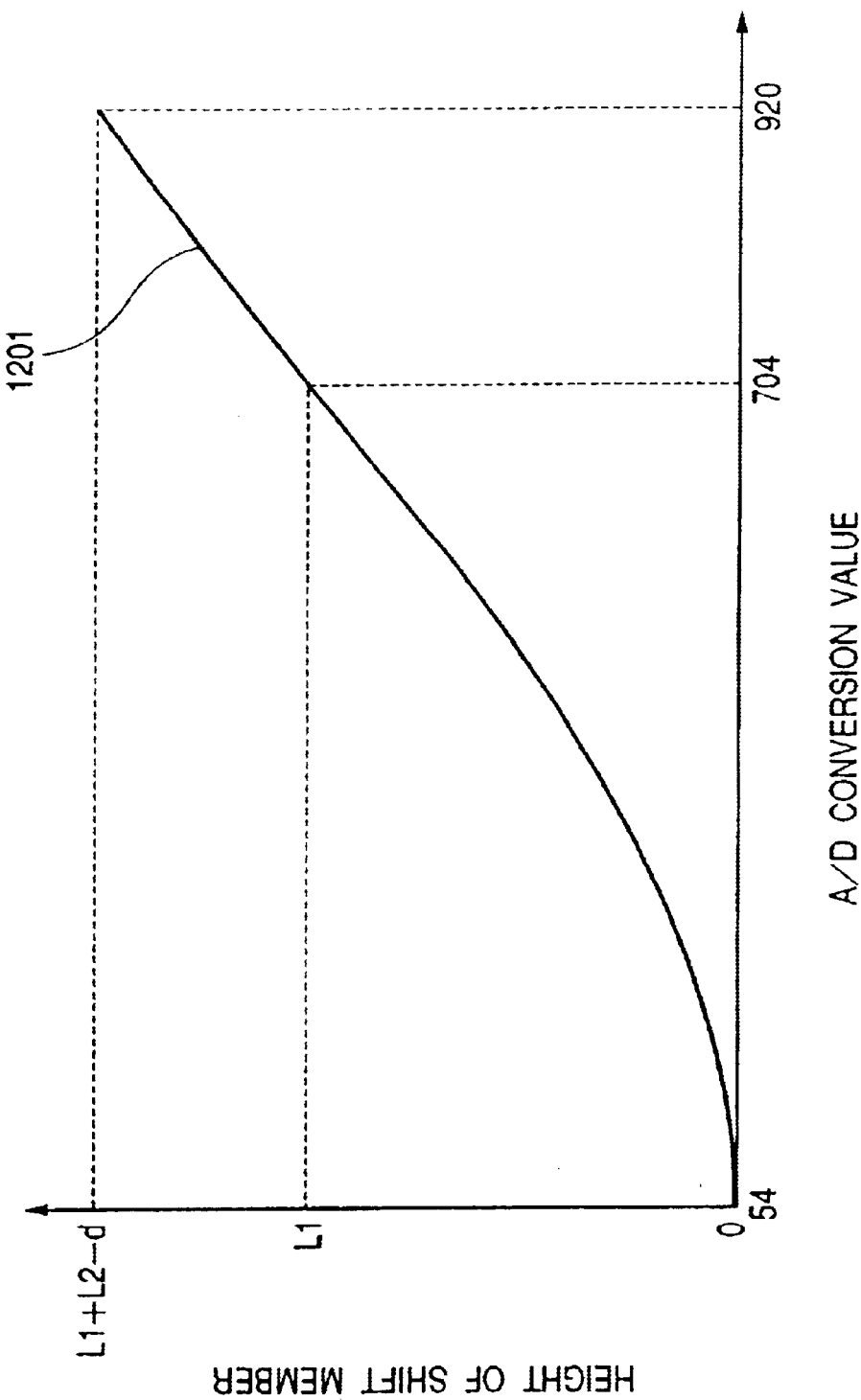
FIG. 12 is a graph showing a conversion curve defining the relationship between the A/D conversion value and the height of the shift member in accordance with the first embodiment of the present invention.
Figure 13:
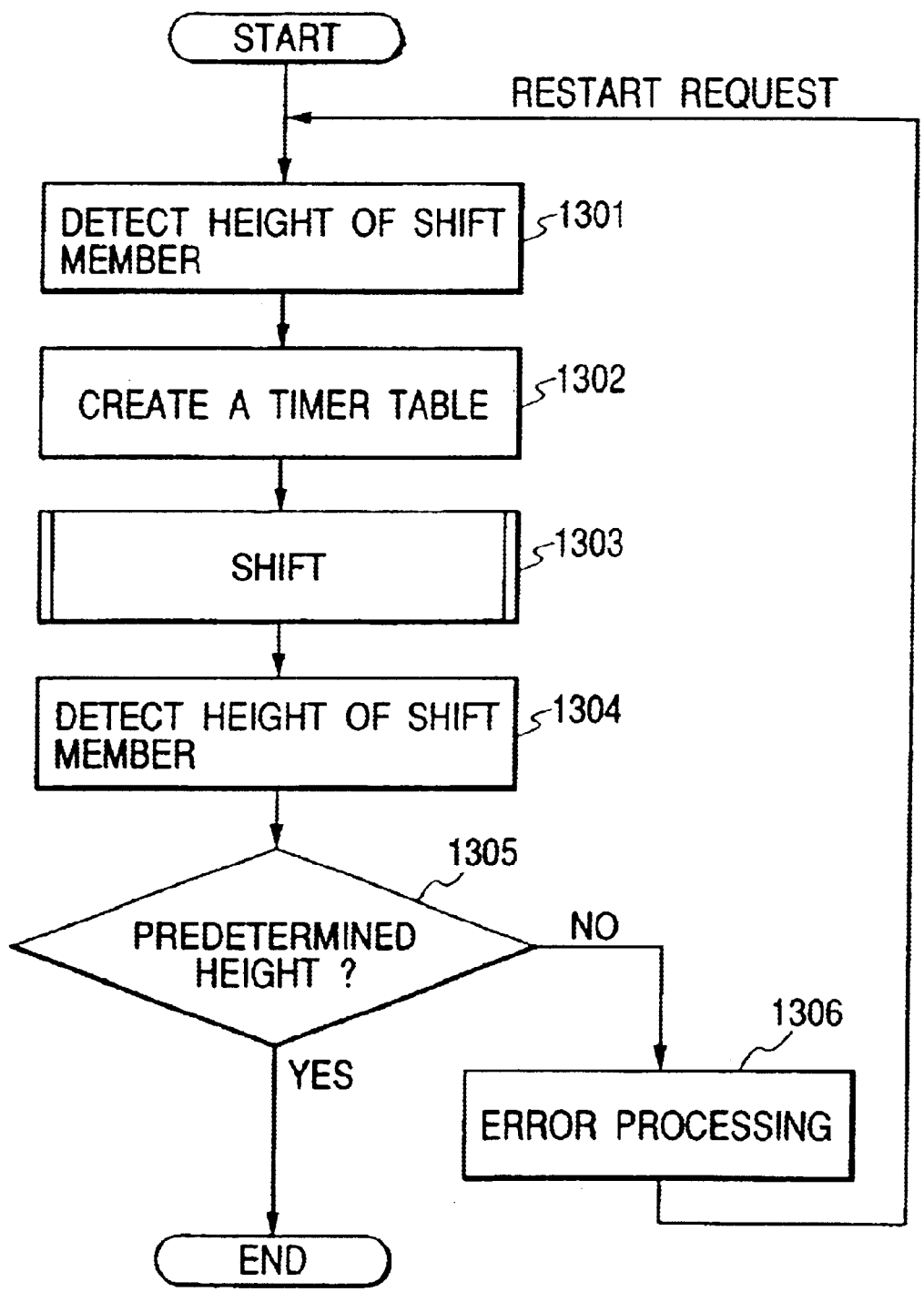
FIG. 13 is a flowchart showing a main routine used in the control of the stepping motors in accordance with the first embodiment of the present invention.

FIG. 13 is a flowchart showing a main routine performed in the MCU 27 during the upward shifting operation of the shift member16. In a step 1301, an analog voltage of the potentiometer is entered into the CPU board 2 and is subjected to the A/D conversion by the A/D converter 75 to produce a digital data. The height of the shift member 16 is then obtained with reference to a conversion curve 1201 shown in FIG. 12.

Next, in a step 1302, a timer value table is created based on the height of the shift member 16 according to the above-described calculation method. In a step 1303, the stepping motors are driven according to the subroutine shown in FIG. 9 to move the shift member 16 in the vertical direction from the start height H2z to the target height H2z. Then, in a step 1304, the analog voltage of the potentiometer is entered again to detect the height of the shift member 16 based on the conversion curve 1201 shown in FIG. 12. In a step 1305, it is checked whether the shift member 16 has reached the target height H2z. When the judgement result is YES in the step 1305, it is concluded that the upward shifting operation is finished. When the shift member 16 has not yet reached the target height (i.e., NO in the step 1305), the control flow proceeds to a step 1306 to perform the error processing. In the error processing, an error message is generated to notify the step out of the stepping motor or the breaking of the timing belts 9 and 11. Then, in response to a restart request, the control flow returns to the step 1301 to execute the above-described steps again.

When the shift member 16 moves in the downward direction or in the horizontal direction, the height of the shift member 16 can be detected based on the signal of the angle sensor 24 in accordance with the procedure similar to the above-described steps 1303 to 1306.

Second Embodiment

Figure 14:
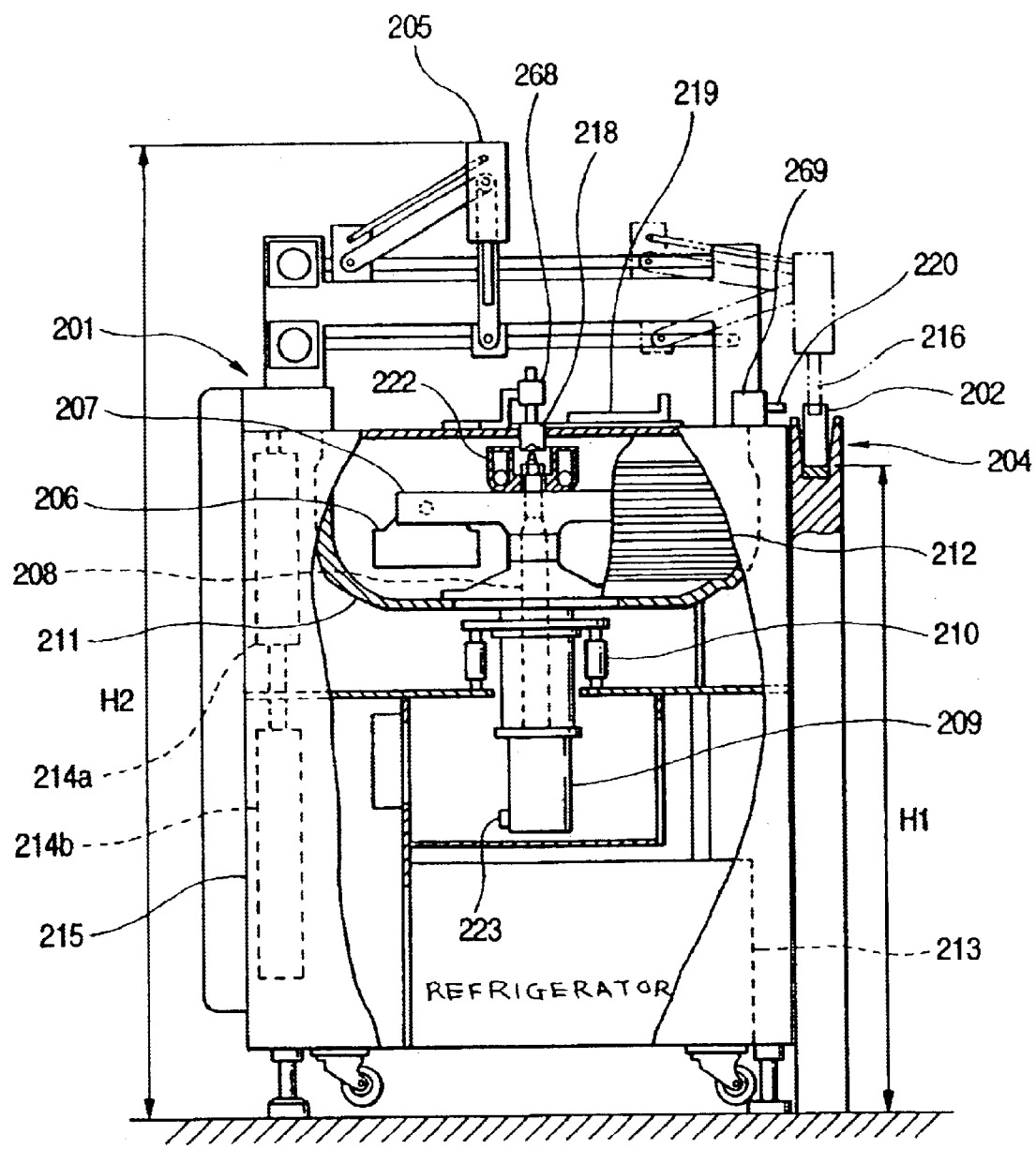
FIG. 14 is a partly sectional side view showing an automatic centrifugal machine in accordance with a second embodiment of the present invention.
Figure 15:
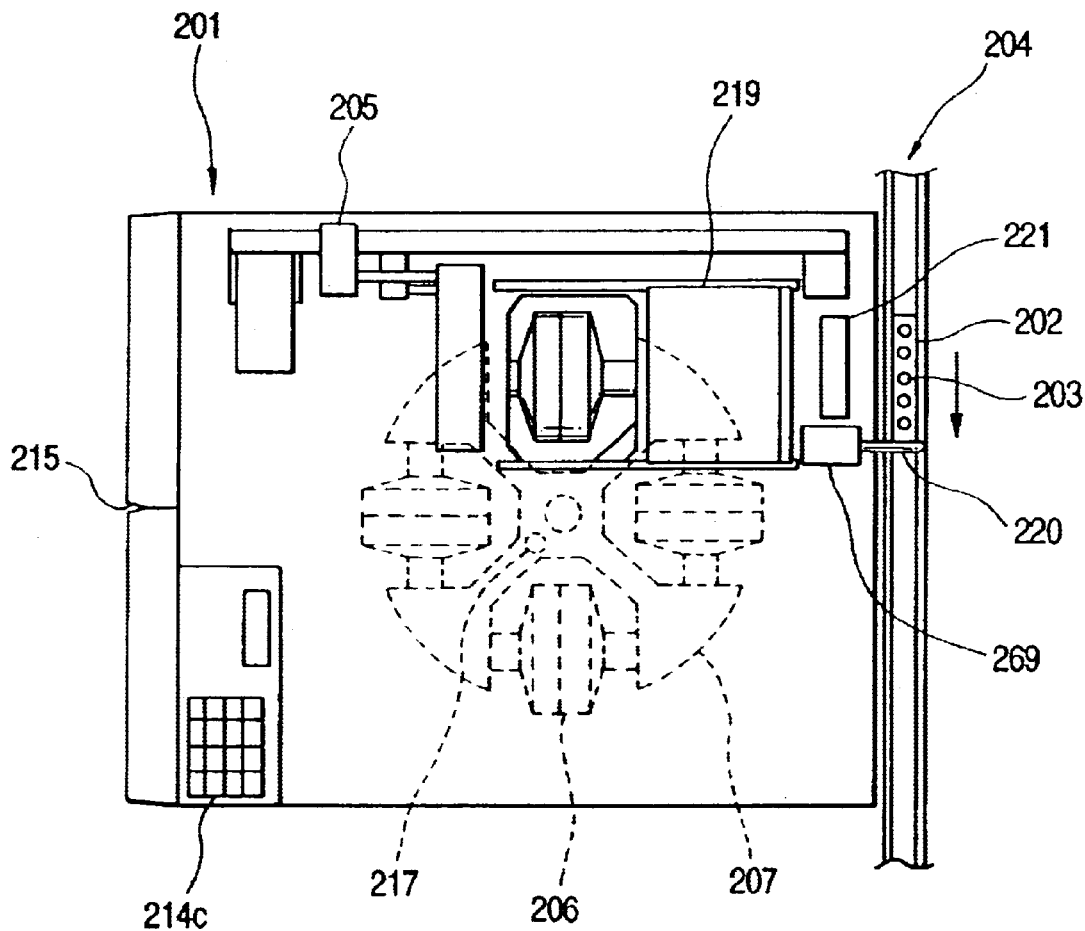
FIG. 15 is a plan view showing the automatic centrifugal machine in accordance with the second embodiment of the present invention.

FIG. 14 is a partly-sectional side view showing an automatic centrifugal machine 201 in accordance with another preferred embodiment of the present invention. FIG. 15 is a plan view showing the automatic centrifugal machine 201. A rack 202 accommodates a total of five test tubes (vacuum tubes) 203 each including a specimen of blood. A conveyor line 204 carries a plurality of racks 202. The automatic centrifugal machine 201 is disposed in the vicinity of the conveyor line 204.

To improve the work efficiency or machine maintenance, the physical size of average workers is considered in determining a height H1 of the conveyor line 204. According to this embodiment, the workers may keep sitting or standing during the work. Hence, the height H1 of the conveyor line 204 is set in a range from 750 mm to 850 mm.

The automatic centrifugal machine 201 comprises a handling apparatus 205 which holds and carries the rack 202, and a rotor 207 combined with a plurality of buckets 206 angularly spaced at equal intervals (e.g., 90 degrees). The rack 202 is placed in the bucket 206 and is subjected to a centrifugal force caused by the rotation of the rotor 207. The rotor 207 is connected via a shaft 208 to a drive motor (e.g., servo motor) 209. The drive motor 209 is supported to a frame via a vibration-proof member 210 to absorb the resonant oscillation. The vibration-proof member 210 consists of a spring and a damper. Furthermore, the automatic centrifugal machine 201 comprises a chamber 211 surrounding the rotor 207, an evaporator pipe 212 wound around the chamber 211 to circulate coolant, a refrigerator 213 supplying the coolant to the evaporator pipe 212, and a controller 214 controlling the handling apparatus 205 and the drive motor 209. The CPU board 214*a* and the driver 214*b* are disposed at a front side so that the operators can easily operate or maintain them when a front cover 215 is opened. Although not shown in FIG. 2, both sides of the automatic centrifugal machine 201 with respect to the conveyor line 204 are occupied by other apparatuses, such as a preprocessing apparatus for a biochemical inspection of the specimen. Thus, the control section is disposed at the front side of the automatic centrifugal machine 201.

The controller 214 comprises the CPU board 214*a,* the driver 214*b,* and an operation panel 214*c*. The substrate of the controller 214 is compact. Thus, the controller 214, installed in an attached case, is portable. For the centrifugal separation of each test specimen, the drive motor 209 rotates the rotor 207 at higher speeds. The chamber 211, surrounding the rotor 207, is refrigerated to suppress the temperature increase of the rotor 207 derived from the frictional rotation. As the side wall of the cylindrical chamber 211 is almost closed by the evaporator pipe 212, it is desirable to select the up-and-down direction for entering or taking the rack 202 into or out of the automatic centrifugal machine 201. Thus, the handling apparatus 205 is disposed above the centrifugal machine 201. To suppress a height H2 of the automatic centrifugal machine 201, the height of the bucket 206 is substantially equalized with the height of the conveyor line 204. The handling apparatus 205 is compact in size and low in height. The height of the drive motor 209 is dependent on the height of the bucket 206. The drive motor 209 is a servo motor which is capable of rotating the rotor 207 at higher speeds and stably positioning the rotor 207. The refrigerator 213 is disposed under the drive motor 209. Preferably, the drive motor 209 is a DC brushless servo motor.

Figure 16:
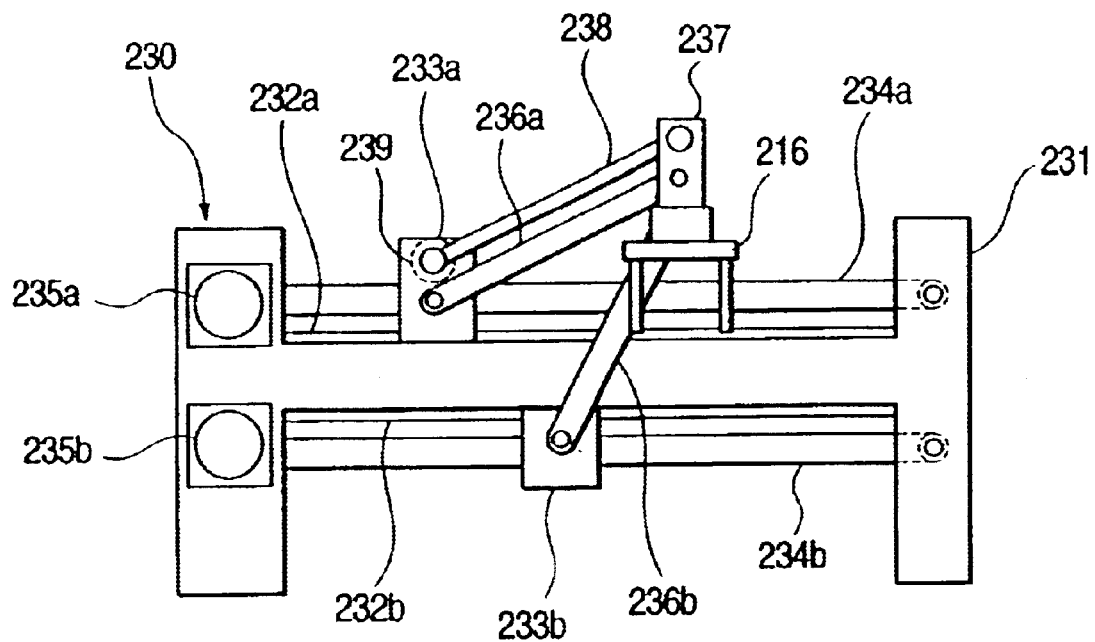
FIG. 16 is a view showing the arrangement of a link arm mechanism in accordance with the second embodiment of the present invention.

The handling apparatus 205 includes a link arm mechanism 230 shown in FIG. 16 which is effective to downsize the size of the apparatus. The link arm mechanism 230 comprises a base 231 having a H-shaped cross section. A first guide member 232a and a second guide member 232b, extending in parallel with each other, are provided on this base 230. A first slider 233a slides on the first guide member 232a. A second slider 233b slides on the second guide member 232b. The first slider 233a is fixed to a timing belt 234a. A stepping motor 235a has an output shaft with a gear or the like (not shown) to entrain the timing belt 234a. The stepping motor 235a, when rotating, shifts the timing belt 234a in the right-and-left direction. In the same manner, the second slider 233b is fixed to a timing belt 234b. A stepping motor 235b has an output shaft with a gear or the like (not shown) to entrain the timing belt 234b. The stepping motor 235b, when rotating, shifts the timing belt 234b in the right-and-left direction.

The first slider 233a supports one end of a first arm 236a so as to allow the first arm 236a to swing pivotally. The second slider 233b supports one end of a second arm 236b so as to allow the second arm 236b to swing pivotally. The other end of the first arm 236a and the other end of the second arm 236b are pivoted at the same axis of the shift member 237. The shift member 237 is equipped with a manipulator hand 216. The first and second sliders 233a and 233b are disposed at one side of the shift member 237. A parallel link 238, disposed in parallel with the first arm 236a, connects the shift member 237 to the first slider 233a. Thus, the shift member 237 is stably held.

An angle sensor 239 is provided coaxially with the pivot axis of the parallel link 238 of the first slider 233a. The angle sensor 239 detects an intersecting angle α between the first arm 236a and the first guide member 232a.

According to the arrangement of the above-described link arm mechanism 230, the stepping motor cables are free from breaking because the stepping motors 235a and 235b are stationarily fixed to the base 231 independently of the shift movement of the sliders 233a, 233b and the shift member 237.

Each of the stepping motors 235a and 235b has an electromagnetic lock braking mechanism capable of locking its rotor shaft under a spring force so as to securely hold the position of the stepping motors 235a and 235b. Thus, it becomes possible to prevent the shift member 237 from falling due to self-weight in case of electric power cut. For easy understanding, the manipulator hand 216 shown in FIG. 15 is drawn at a 90-degree rotated position.

By adopting the handling apparatus 205 employing the above-described link arm mechanism 230, the overall height H2 of the automatic centrifugal machine 201 is suppressed within 1,450 mm which is an eye height of an average woman operator.

Figure 17:
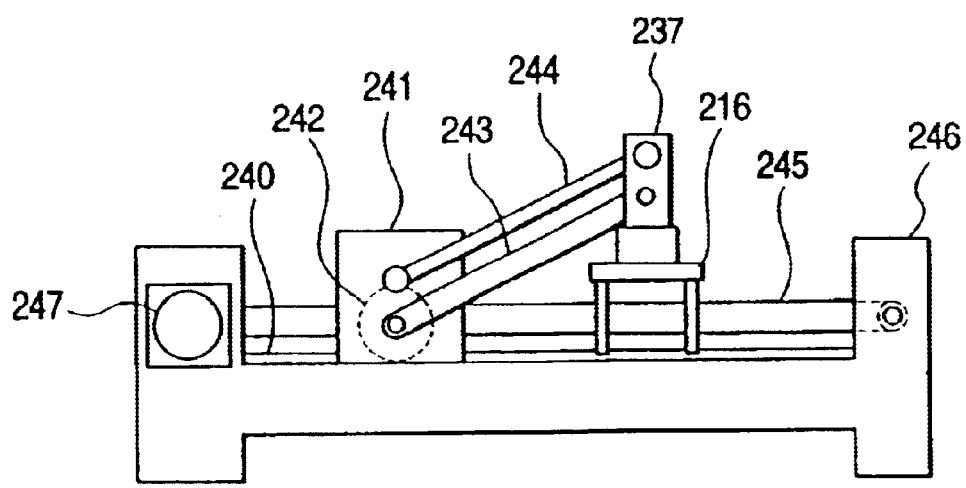
FIG. 17 is a view showing the arrangement of another link arm mechanism in accordance with the second embodiment of the present invention.

FIG. 17 shows another arrangement of the handling apparatus 205 which comprises a single guide member 240, a single slider 241 shiftable along the guide member 240, and an arm-driving stepping motor 242 driving an arm 243. One end of the arm 243 is fixedly pivoted to the output shaft of the stepping motor 242 so that the arm 243 can swing about the output shaft of the stepping motor 242. The other end of the arm 243 is pivotally connected to the shift member 237 equipped with the manipulator hand 216.

A parallel link 244, disposed in parallel with the arm 243, connects the shift member 237 to the slider 241. Thus, the shift member 237 is stably held. The slider 241 is fixed to a timing belt 245. A belt-driving stepping motor 247, stationarily fixed to a base 246, has an output shaft with a gear or the like (not shown) to entrain the timing belt 245. The stepping motor 247, when rotating, shifts the timing belt 245 in the right-and-left direction. With this arrangement, it becomes possible to realize a compact handling apparatus 205 having two degrees of freedom which provides a wide movable range.

Figure 18:
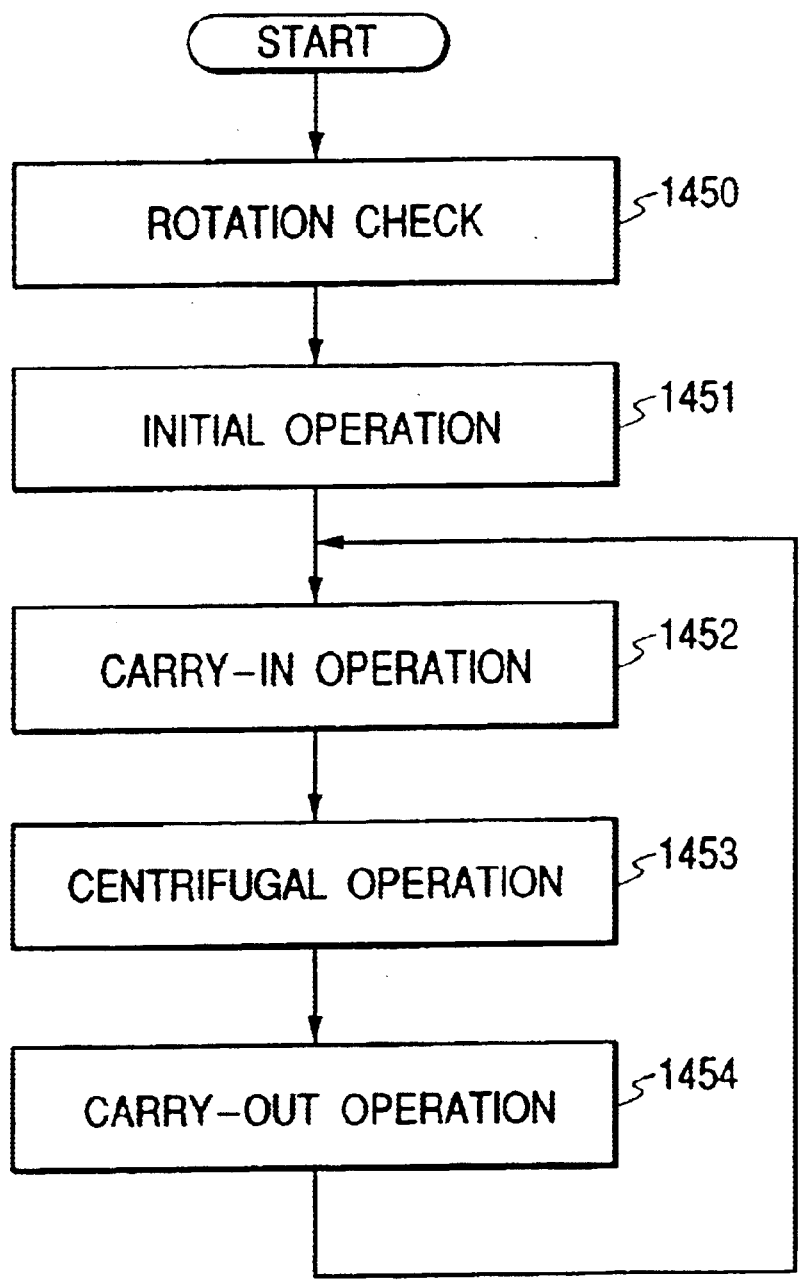
FIG. 18 is a flowchart showing the operation of the automatic centrifugal machine in accordance with the second embodiment of the present invention.
Figure 19:
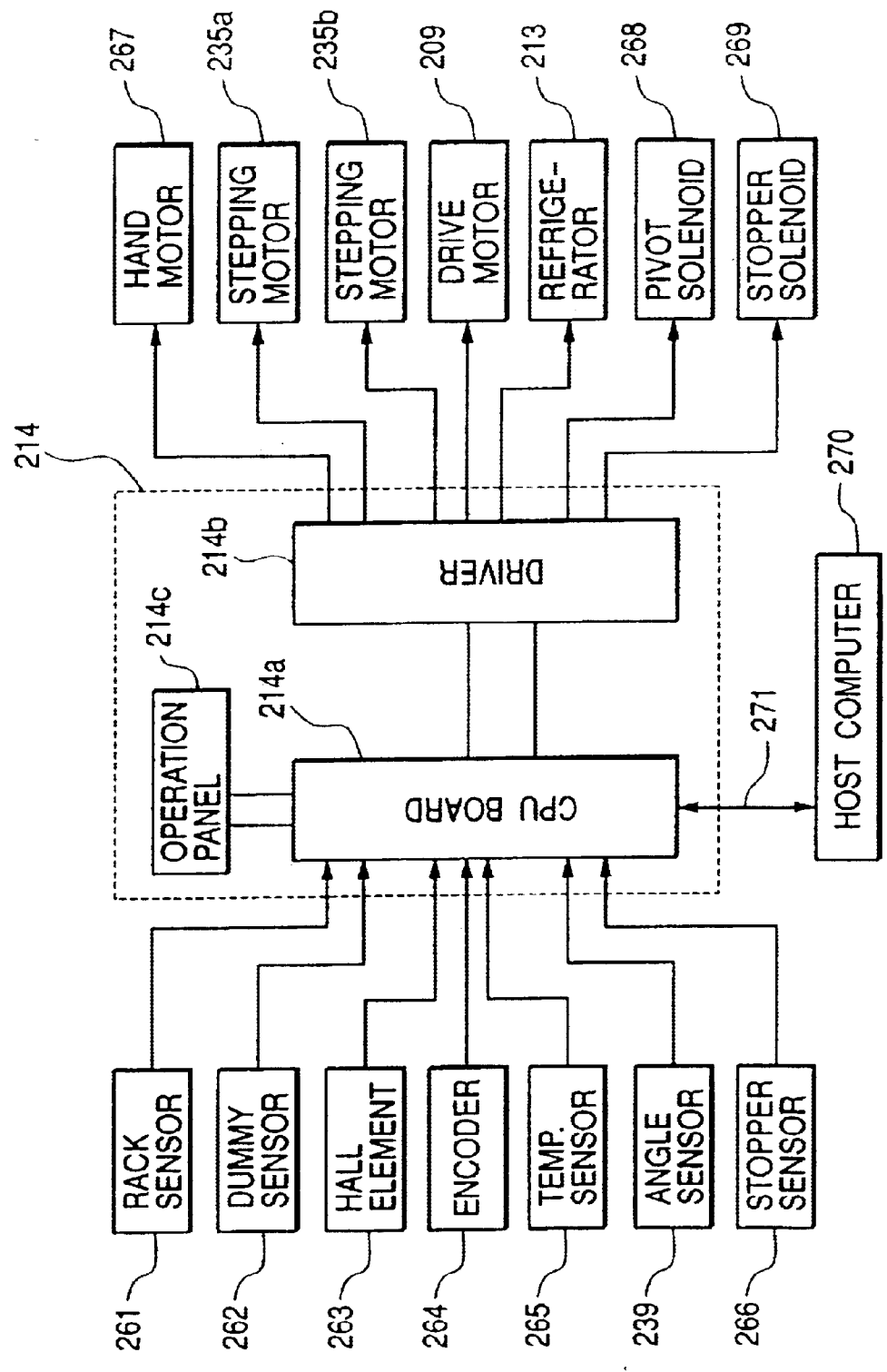
FIG. 19 is a circuit block diagram showing a control system in accordance with the second embodiment of the present invention.

The above-described automatic centrifugal machine 201 operates in accordance with the flowchart shown in FIG. 18. After, the controller 214 of the automatic centrifugal machine 201 starts its operation in response to the power supply. In a step 1450, it is checked whether the rotor 207 is rotating. The rotation of the rotor 207 can be detected by counting the pulse generated from an encoder 264 of the drive motor 209. Meanwhile, a magnet 217 is integrally provided in the rotor 207. A Hall element 263, interactive with the magnet 217, generates a pulse signal in response to the rotation of the rotor 207. The frequency of the generated pulse signal is converted into a voltage signal, from which the rotation of the rotor 207 can be detected. When the rotation of the rotor 207 is detected from either of the above-described rotation sensing mechanisms, a braking force is applied to the drive motor 209 to stop the rotation of the rotor 207. When the rotor 207 is not rotating, the controller 214 waits an initial operation command coming from a host computer (i.e., an external control device) 270 connected via a RC232C communication cable 271.

Upon receiving the initial operation command generated from the host computer 270, an initial operation is performed in a step 1451. More specifically, a pivot solenoid 268 is energized to move a pivot 218 downward. The pivot 218 is positioned just above the center of the rotor 207. The pivot 218, when lowered, corrects the inclination of the rotor 207. Subsequently, the stepping motors 235a and 235b are activated to release the electromagnetic lock. The link arm mechanism 230 starts an origin returning operation which is performed in the following manner.

The height of the manipulator hand 216 is obtained based on the angle α detected by the angle sensor 239 and the length of the first arm 236a. Then, the behaviors of the sliders 233a and 233b are respectively calculated to realize a vertical lifting of the manipulator hand 216. Based on the calculated drive pulse rates, the stepping motors 235a and 235b are driven to shift the manipulator hand 216 upward. It is then checked, with reference to the angle signal of the angle sensor 239, whether the manipulator hand 216 has reached a target height. After completing the confirmation, the sliders 233a and 233b are simultaneously shifted at the same speed toward the origin sensor (not shown). Thus, the link arm mechanism 230 is returned to the origin, and the origin returning operation is completed.

Figure 20:
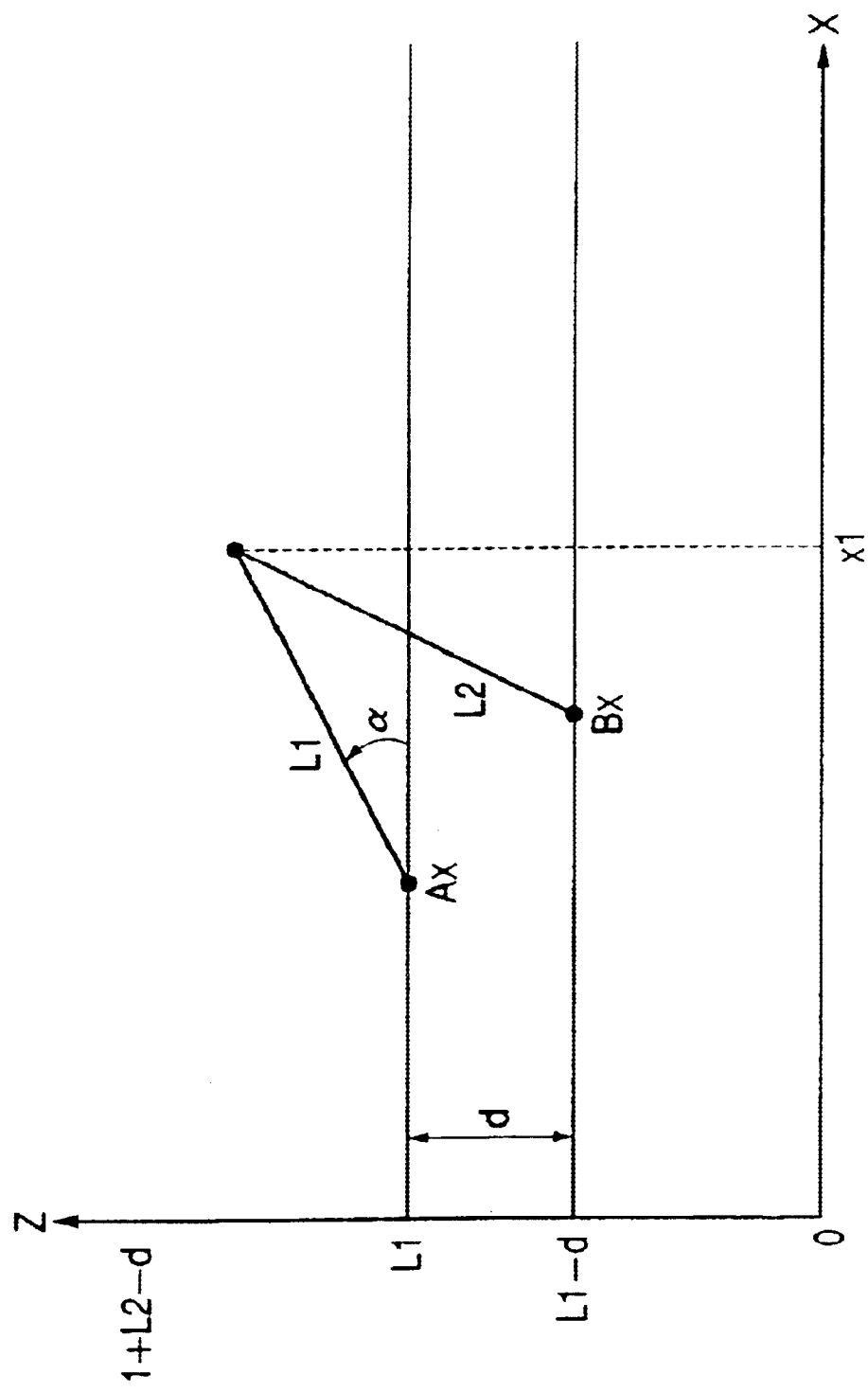
FIG. 20 is a coordinate view illustrating the operation of the link arm mechanism in accordance with the second embodiment of the present invention.

Hereinafter, the operation of the above-described link arm mechanism 230 will be explained with reference to the two-dimensional (orthogonal) coordinate system shown in FIG. 20, wherein an X axis represents the right-and-left direction and a Z axis represents the up-and-down direction.

The vertical shifting operation of the manipulator hand 216 can be realized by controlling the first slider 233a and the second slider 233b so as to satisfy the following equation.

$$Bx = x1 - \sqrt{L2^2 - \left[L1\sin\left\{\cos^{-1}\left(\frac{x1-Ax}{L1}\right)\right\} + d\right]^2} \qquad (7)$$

where "L1" represents the length of the first arm 236a, "L2" represents the length of the second arm 236b, "d" represents the clearance between the arm pivot axes on the first slider 233a and the second slider 233b, "Ax" represents the position of the first slider 233a in the sliding direction and "Bx" represents the position of the second slider 233b in the sliding direction, and "x1" represents the position of the shift member 237 in the sliding direction.

The drive motor 209 is controlled in the following manner. Using A-phase, B-phase, and Z-phase signals of the rotary encoder 264, a NAND logic circuit a trigger signal of one pulse per rotation. The rotational pulse signal of the encoder 264 is fed back at predetermined intervals to calculate command data (i.e., a target rotational angle and a target angular speed) of the drive motor 209. Based on the difference between the calculated command values and actual data, a PID control data is obtained. The PID control data generally consists of proportional, integral and differential elements. Then, referring to the PID control data thus obtained, the drive motor 209 is driven by the PWM (i.e., pulse width modulation) control.

The thus controlled drive motor 209 rotates the rotor 207 at a low speed of around 20 min$^{-1}$ until the rotor 207 reaches a loading position for the rack 202 which is predesignated with respect to the trigger signal.

A counter IC (not shown), counting the pulses generated from the encoder 264, is cleared in response to each entry of the trigger signal. To avoid any interference between the link arm mechanism 230 and the drive motor 209, the rotation of the rotor 207 is controlled after finishing the lifting operation of the manipulator hand 216.

After finishing the origin returning operation, a door 219 is opened by the manipulator hand 216. The door 219 is located above the rotor 207. To check the presence of the rack 202 in the bucket 206, the manipulator hand 216 is lowered and closed to perform the operation for searching the rack 202. A hand motor 267 is linked via a cam mechanism (not shown) to the manipulator hand 216 to control the closing of the manipulator hand 216. When the manipulator hand 216 is shifted down toward the bucket 206, the manipulator hand 216 intentionally hits the periphery of the bucket to correct the position of the bucket 206 if the bucket 206 inclines from a horizontally balanced position after finishing a swing operation.

To shift the manipulator hand 216 downward, the required pulse rates of the stepping motors 235a and 235b are calculated beforehand and memorized. Each of the stepping motors 235a and 235b is driven by successively reading out the memorized pulse rates. Subsequently, the manipulator hand 216 shifts laterally to a rack unloading position and closes its grip. A rack sensor 261, equipped in the manipulator hand 216, detects the rack 202 if it is held by the manipulator hand 216. When any rack 202 is held by the manipulator hand 216, the manipulator hand 216 shifts upward and places the rack 202 on the conveyor line 204 in accordance with the command of the host computer 270. When no rack 202 is detected in the manipulator hand 216, the manipulator hand 216 shifts upward to perform the positioning operation for the manipulator hand 216 and the rotor 207. In every stop position of the manipulator hand 216, it is checked whether the difference between the actual data of the angle α detected by the angle sensor 239 and the calculated data is within a predetermined allowable range. Based on this comparison, the step out of respective stepping motors 235a and 235b is detected. The lowering operation of the manipulator hand 216 along the bucket periphery is performed once for each bucket 206 to taking out every rack 202. After confirming the absence of the rack 202 in each bucket 206, the controller 214 waits for the next carry-in operation.

In a step 1452 shown in FIG. 18, the controller 214 performs the carry-in operation in response to a command (i.e., a carry-in operation command) sent from the host computer 270. First, a stopper solenoid 269 is energized to activate a stopper 220 which stops the rack 202 carrying specimens flowing along the conveyor line 204. Then, the manipulator hand 216 shifts to the conveyor line 204 to pick the rack 202 up, and then moves above the bucket 206. On the other hand, the drive motor 209 positions the rotor 207 at a rack loading position. The manipulator hand 216 is lowered to place the rack 202 in the bucket 206. By repeating this operation, a required number of racks 202 are loaded in the bucket 206. In view of keeping the weight balance, each even-number rack 202 is placed in an opposed bucket 206 which is angularly spaced by 180° about the axis of the rotor 207 from the bucket 206 of an odd-number rack 202 loaded immediately before. The stopper 220 is kept at a retracted position when it is not operated. A stopper sensor 266 always monitors the stopper 220 which may accidentally protrude toward the conveyor line 204.

Next, in a step 1453, the controller 214 performs a centrifugal operation in response to a command (i.e., a centrifugal operation command) sent from the host computer 270. When the total number of the loaded racks 202 is odd number, a dummy rack 221 is placed in an appropriate bucket 206 to improve the weight balance during the centrifugal operation. In this case, the dummy rack 221 has an average weight of the loaded racks 202. As shown in FIGS. 14 and 15, the rack 202 on the conveyor line 204 stopped by the stopper 220, the dummy rack 221, and the bucket 206 loading the rack 202 are aligned at substantially the same height along a line normal to the conveyor line 204. This arrangement allows the carry-in or carry-out operation with the handling apparatus 205 having two degrees of freedom.

The dummy rack 221 and each rack 202 are different in shape. A dummy sensor 262 discriminates them based on a closed angle of the manipulator hand 216 which varies according to the difference of the rack configuration. To prevent the door 219 from floating by the air pressure caused during the centrifugal operation, the manipulator hand 216 is placed on the door 219. In this case, no exciting current is supplied to the stepping motors 235a and 235b. The manipulator hand 216 falls due to its self-weight until it lands on the door 219. Then, the electromagnetic lock current for each stepping motor is controlled to lock the rotational shaft of each stepping motor. The locked manipulator hand 216 securely holds the door 219.

Subsequently, the power supply to the pivot solenoid 268 is stopped. The pivot solenoid 268 is positioned just above the center of the rotor 207. Upon deactivation of the pivot solenoid 268, the pivot 218 is returned upward by a spring force. Thereafter, the drive motor 209 is rotated to execute the centrifugal separation of each test specimen. During an acceleration of the drive motor 209, a constant current is supplied to the drive motor 209 until the rotation of the drive motor 209 reaches a target speed of, e.g., 3,000 min$^{-1}$.

Figure 21:
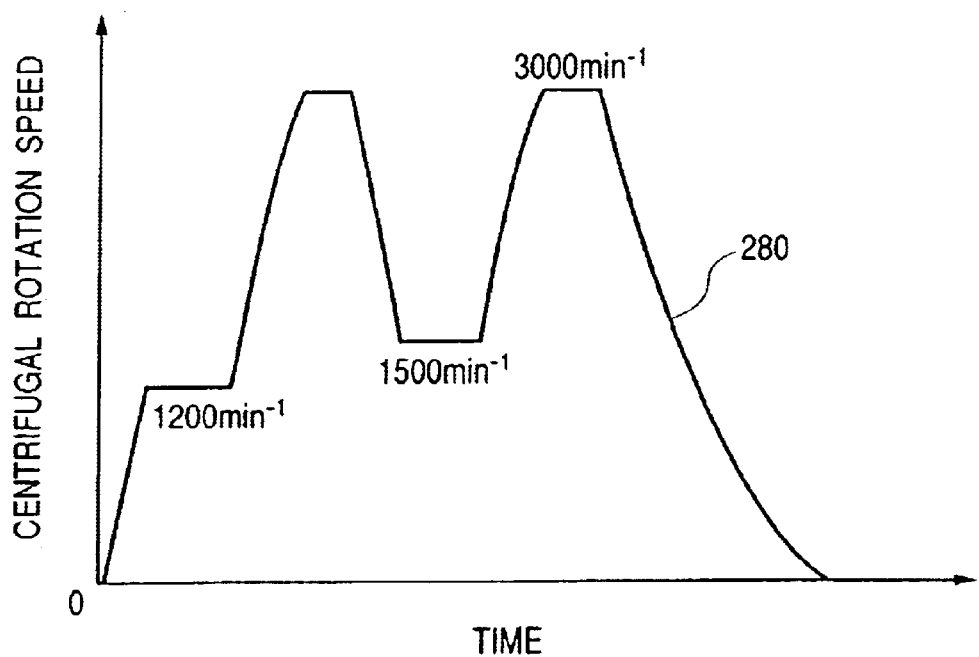
FIG. 21 is a graph showing rotational speed control in a centrifugal operation in accordance with the second embodiment of the present invention.

To perform the centrifugal operation, the drive motor 209 is driven at this target speed for a predetermined centrifugal time, e.g., five minutes. Then, the drive motor 209 is decelerated. There is three kinds of deceleration methods for avoiding contamination of the centrifuged test sample. A first one is a natural deceleration method for naturally decelerating the drive motor 209 by the aerodynamic or mechanical friction under the condition where no electric power is supplied to the drive motor 209. A second one is an ordinary deceleration method for promptly decelerating the drive motor 209 in a high-speed region by using the regenerative braking and then slowly decelerating in a low-speed region. A third one is a parabolic deceleration method for decelerating the drive motor 209 along a parabolic speed curve. According to the natural deceleration method and the parabolic deceleration method, the rotor 207 is once stopped and is then rotated at a very slow speed to bring the rack 202 to a predetermined unloading position. According to the ordinary deceleration method, the rotational speed control is switched to a positional control when the rotational speed of the rotor 207 is reduced to a predetermined value, e.g., 20 $min^{-1}$. According to the positional control, the rack 202 is positioned to the predetermined unloading position without once stopping the rotor 207. Furthermore, it is possible to realize a stepwise centrifugal operation according to an arbitrary centrifugal speed curve, e.g., a curve 280 shown in FIG. 21, so as to allow a setting of an optimum centrifugal operation. The above-described deceleration method or the stepwise centrifugal operation is designated by a command sent from the host computer 270. The automatic centrifugal machine 201 operates in accordance with this command.

Although the dummy rack 221 is used to improve the weight balance during the centrifugal operation, the automatic centrifugal machine 201 allows the centrifugal separation of a single test tube 203 without using the dummy rack 221. To realize this, a ball balancer 222 is provided at an upper portion of the rotor 207. A movable ball included in the ball balancer 222 adjusts the weight balance. An accelerator sensor 223, provided at a lower portion of the drive motor 209, detects an abnormal vibration of the drive motor 209. When the acceleration signal of the accelerator sensor 223 exceeds a predetermined value, the drive motor 209 is braked to stop the rotor 207.

After finishing the centrifugal operation, in a step 1454 shown in FIG. 18, the controller 214 performs a carry-out operation in response to a command (i.e., a carry-out operation command) sent from the host computer 270. First, the pivot solenoid 268 is energized to lower the pivot 218 to correct the inclination of the rotor 207. The stepping motors 235a and 235b are activated to release the electromagnetic lock. The manipulator hand 216 is lifted to a predetermined height to perform the origin returning operation. Thereafter, the door 219 provided above the rotor 207 is opened by the manipulator hand 216. The manipulator hand 216 shifts above the periphery of the bucket 206 and then hits the bucket 206 to correct the position of the bucket 206 if the bucket 206 inclines from a horizontally balanced position. After correcting the inclination, the manipulator hand 216 shifts the rack 202 laterally to the unloading position. Then, the manipulator hand 216 holds the rack 202 to lift it up and place it on the conveyor line 204. In the same manner as the initial operation, the inclination correcting operation is performed once for each bucket 206. Subsequently, the rack 202 designated by the host computer 270 is carried out of the rack 206. The carry-out operation is performed in the following manner.

The host computer 270 flexibly determines the carry-out order. For example, it is possible to perform the carry-out operation of the racks 202 according to the carry-in order and loaded placed memorized in a memory of the CPU board 214a. After finishing the carry-out operation of all of the racks 202, the dummy rack 221 is returned to its home position. Then, the controller 214 waits for the next carry-in operation command to be generated from the host computer 270 and repeats the above-described carry-in, centrifugal, and carry-out operations defined by the steps 1452 to 1454 shown in FIG. 18.

Figure 22:
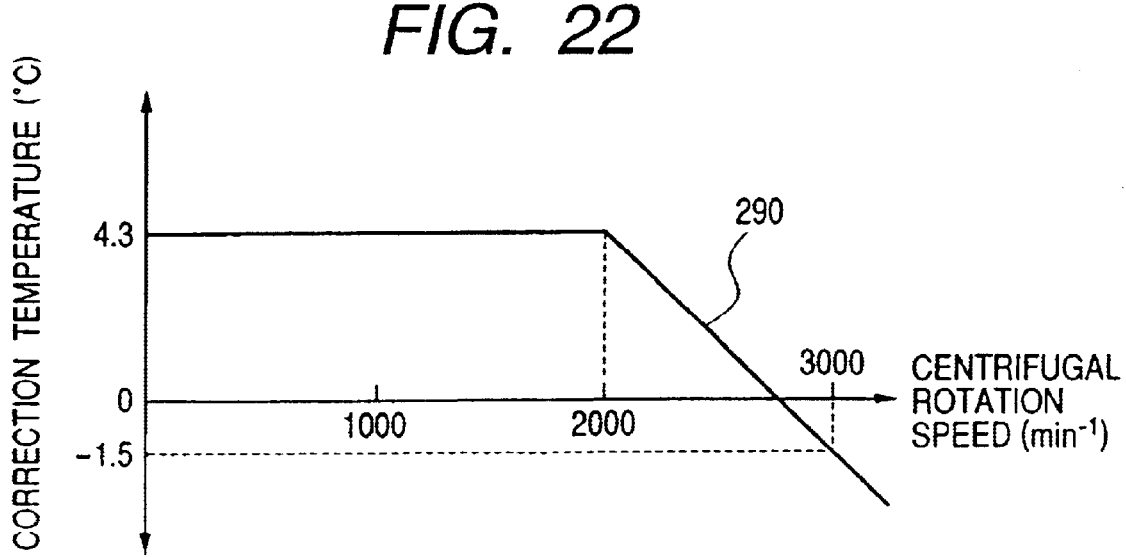
FIG. 22 is a graph showing a temperature correction curve used in the temperature control in accordance with the second embodiment of the present invention.

During the above-described operation of the drive motor 209, the temperature of the chamber 211 is maintained within a predetermined range. A thermistor (not shown) is provided at a lower portion of the chamber 211. A resistance value of the thermistor is converted into a temperature change. The refrigerator 213 is on-and-off controlled based on the difference between a set temperature designated from the host computer 270 and the sensed actual temperature. The set temperature is selectable in the range from 10° C. to 30° C. by the increments of 0.1° C. The temperature control method used in the centrifugal operation differs from that used in other operations. During the operations other than the centrifugal operation, the refrigerator 213 is turned on until the temperature at the lower portion of the chamber 211 decreases to −3 degrees with respect to the set temperature, and is turned off for 120 seconds or more. Subsequently, when the temperature increases to a level of −1 degree with respect to the set temperature, the refrigerator 213 is turned on for 40 seconds or more until the temperature decreases to −3. The temperature control operation is repeated in this manner. During the centrifugal operation, the refrigerator 213 is turned on until the temperature at the lower portion of the chamber 211 decreases to −5 degrees with respect to the set temperature, and is turned off for 120 seconds or more. Subsequently, when the temperature increases to a level of −3 degrees with respect to the set temperature, the refrigerator 213 is turned on for 40 seconds or more until the temperature decreases to −5. Furthermore, a correction temperature value 290 is added to the set temperature to correct the controlled target temperature. As shown in FIG. 22, the correction temperature value 290 is 4.3 degrees in the range lower than 2,000 $min^{-1}$ and decreases with a gradient of −5.8/1,000 (degree/$min^{-1}$). The correction temperature value 290 is determined to correct the heat generation of the test specimen in a high-speed region. According to the above-described temperature control method, the refrigerator 213 is on-off controlled so as to maintain the temperature of the test specimen within a predetermined range.

What is claimed is:

1. A control method for a link arm mechanism, said link arm mechanism comprising:
   a first guide member and a second guide member disposed in parallel with each other;
   a first slider shiftable along said first guide member;
   a second slider shiftable along said second guide member;
   a first arm having a length longer than a clearance between axes of said first guide member and said second guide member, with one end pivotally supported by said first slider;
   a second arm having a length longer than the clearance between the axes of said first guide member and said second guide member, with one end pivotally supported by said second slider; and
   a shift member supported by the other ends of said first and second arms and supporting a working device,
   and said control method comprising the step of:
   shifting said shift member along a line normal to the sliding direction of said first and second sliders by controlling the sliding positions of said first and second sliders so as to satisfy the following relationship $$Bx = xl - \sqrt{L2^2 - \left[Ll \sin\left\{\cos^{-1}\left(\frac{xl - Ax}{Ll}\right)\right\} + d\right]^2}$$

where "L1" represents the length of said first arm, "L2" represents the length of said second arm, "d" represents the clearance between the arm pivot axes on said first slider and said second slider, "Ax" represents the position of said first slider in said sliding direction and "Bx" represents the position of said second slider in said sliding direction, and "x1" represents the position of said shift member in said sliding direction.

2. The control method for a link arm mechanism in accordance with claim 1, wherein said control step for shifting said shift member comprises a calculating step for obtaining a target speed curve of said first slider and a target speed curve of said second slider based on a target speed curve of said shift member.

3. The control method for a link arm mechanism in accordance with claim 1, wherein an angle sensor is provided at least at one of said first and second sliders to detect the shifting position of said shift member based on a detected angle of said angle sensor.

4. The control method for a link arm mechanism in accordance with claim 3, wherein said control step for shifting said shift member is performed periodically, and said detection of the shifting position of said shift member is performed at least before or after each shifting operation of said shift member.

* * * * *